US012582790B2

(12) United States Patent
Bechtel et al.

(10) Patent No.: US 12,582,790 B2
(45) Date of Patent: Mar. 24, 2026

(54) RESPIRATORY MASK WITH GUIDE REGION

(71) Applicant: Loewenstein Medical Technology S.A., Luxembourg (LU)

(72) Inventors: Martin Bechtel, Winsen/Luhe (DE); Arnold Frerichs, Buxtehude (DE); Joachim Gardein, Tenerife/Canary Islands (ES)

(73) Assignee: LOEWENSTEIN MEDICAL TECHNOLOGY S.A., Luxembourg (LU)

( * ) Notice: Subject to any disclaimer, the term of this patent is extended or adjusted under 35 U.S.C. 154(b) by 975 days.

(21) Appl. No.: 17/658,326

(22) Filed: Apr. 7, 2022

(65) Prior Publication Data

US 2022/0323707 A1      Oct. 13, 2022

(30) Foreign Application Priority Data

Apr. 9, 2021    (DE) .......................... 102021001835.4

(51) Int. Cl.
*A61M 16/06*            (2006.01)
(52) U.S. Cl.
CPC .... *A61M 16/0683* (2013.01); *A61M 16/0655* (2014.02)

(58) Field of Classification Search
CPC .......... A61M 16/0683; A61M 16/0655; A61M 16/0605; A61M 16/0633; A61M 16/06; A62B 18/02; A62B 18/025; A62B 18/08; A62B 18/084
See application file for complete search history.

(56) References Cited

U.S. PATENT DOCUMENTS

| | | | |
|---|---|---|---|
| 2006/0201514 A1 | 9/2006 | Jones et al. | |
| 2009/0173343 A1* | 7/2009 | Omura .............. | A61M 16/0683 |
| | | | 128/205.25 |
| 2010/0154798 A1* | 6/2010 | Henry ................. | A61M 16/065 |
| | | | 128/206.24 |
| 2011/0259337 A1 | 10/2011 | Hitchcock et al. | |
| 2020/0155778 A1 | 5/2020 | Kuriger | |

FOREIGN PATENT DOCUMENTS

| | | |
|---|---|---|
| DE | 102005041716 A1 | 4/2006 |
| DE | 202004021829 U1 | 5/2011 |
| DE | 202005021927 U1 | 6/2011 |
| WO | 2017068530 A2 | 4/2017 |

* cited by examiner

*Primary Examiner* — Margaret M Luarca
(74) *Attorney, Agent, or Firm* — Abel Schillinger, LLP

(57) ABSTRACT

Respiratory mask with a face part which comprises at least one plane of symmetry, a circumferential seal and an outlet, wherein the face part has an outer side with at least two anchor points, which are arranged to both sides of the plane of symmetry, and wherein the at least two anchor points each comprise a receiving element for releasable connection to a connection element, and wherein the connection element is configured to receive a harness. At least one guide region is arranged adjacent to the receiving element.

17 Claims, 21 Drawing Sheets

Figure 1

RESPIRATORY MASK WITH GUIDE REGION

CROSS-REFERENCE TO RELATED APPLICATIONS

The present application claims priority under 35 U.S.C. § 119 of German Patent Application No. 102021001835.4, filed Apr. 9, 2021, the entire disclosure of which is expressly incorporated by reference herein.

BACKGROUND OF THE INVENTION

1. Field of the Invention

The present invention relates to a respiratory mask with guide region.

2. Discussion of Background Information

Respiratory masks are used for ventilation, for respiratory assistance or as protective masks against aerosols composed of solid or liquid particles. A wide variety of materials are used for respiratory masks, these materials being permeable or impermeable to gas. Respiratory masks made of gas-impermeable material have a region which is partially made of a gas-permeable material or which has an outlet for a hose attachment system for inhalation and/or exhalation.

Respiratory masks for ventilation or respiratory assistance form the interface between a user or patient and a ventilator and have to satisfy strict requirements as regards stability, safety and comfort and at the same time must be easy to handle. Respiratory masks are usually fixed on the head of the user or patient via a harness. Particularly in the case of ventilation performed at home, it is the user who is responsible for correctly fitting and fixing the respiratory mask on the face. Coupling the harness to the respiratory mask is usually done via several coupling points and in some cases places high demands on the dexterity of the user or the patient. Correct fastening of the respiratory mask via the harness is a prerequisite for safe and efficient ventilation.

It would therefore be advantageous to have available a respiratory mask that can be easily and securely fitted in place.

SUMMARY OF THE INVENTION

The invention relates to a respiratory mask with a face part which comprises at least one plane of symmetry, a circumferential seal and an outlet, wherein the face part has an outer side with at least two anchor points, which are arranged to both sides of the plane of symmetry, and wherein the at least two anchor points each comprise a receiving element for releasable connection to a connection element, and wherein the connection element is configured to receive a harness. At least one guide region is arranged adjacent to the receiving element.

The respiratory mask is alternatively also characterized in that the guide region is configured for guiding the connection element to the receiving element.

The respiratory mask is alternatively also characterized in that the guide region is arranged to both sides of the plane of symmetry on the face part.

The respiratory mask is alternatively also characterized in that the guide region is formed by a depression in and/or by elevations on the outer side of the face part.

The respiratory mask is also alternatively characterized in that the guide region is configured as a guide groove, wherein the guide groove is formed by a depression.

The respiratory mask is alternatively also characterized in that the guide groove extends over 5% to 100% of the length of the face part, preferably over 50% to 100%, for example over 95% of the length of the face part.

The respiratory mask is alternatively also characterized in that the guide groove comprises a groove inlet which, through a successive depression, forms a transition from the outer side to the final depression.

The respiratory mask is alternatively also characterized in that the groove inlet is arranged at an upper end of the face part.

The respiratory mask is alternatively also characterized in that the guide groove comprises a groove bottom, a rear groove edge, a front groove edge and an end region, wherein the end region is a region of the groove bottom that is enclosed by at least one of the groove edges The respiratory mask is alternatively also characterized in that the surface of the groove bottom is smooth and/or structured.

The respiratory mask is alternatively also characterized in that the surface of the groove edges is smooth and/or structured.

The respiratory mask is alternatively also characterized in that the guide groove is laterally delimited by the groove edges, wherein the groove edges are arranged between the outer side and the groove bottom.

The respiratory mask is alternatively also characterized in that the groove edges are designed extending in a straight line or a curve from the outer side to the groove bottom.

The respiratory mask is alternatively also characterized in that the rear groove edge is arranged with an angle $\alpha 1$ to the groove bottom, and the front groove edge is arranged with an angle $\alpha 2$ to the groove bottom, wherein the values of the angles $\alpha 1$, $\alpha 2$ can be chosen independently of one another.

The respiratory mask is alternatively also characterized in that the transition from the groove bottom to the groove edges has a polygonal and/or rounded shape.

The respiratory mask is alternatively also characterized in that that the rear groove edge is arranged with an angle $\beta 1$ to the outer side, and the front groove edge is arranged with an angle $\beta 2$ to the outer side, wherein the values of the angles $\beta 1$, $\beta 2$ can be chosen independently of one another.

The respiratory mask is alternatively also characterized in that the transition from the outer side to the groove edges has a polygonal and/or rounded shape.

The respiratory mask is alternatively also characterized in that the groove edges are of constant and/or varying height.

The respiratory mask is alternatively also characterized in that the depression of the guide groove is of constant and/or varying depth, wherein the depression has a depth in a range from 0.5 mm to 6 mm.

The respiratory mask is alternatively also characterized in that the depression is of varying depth, wherein the depression in the end region is between 1 mm and 6 mm deep, preferably 4 mm deep, wherein the depression in the other regions of the guide groove is substantially 0.8 mm to 2 mm deep, preferably 1 mm deep.

The respiratory mask is alternatively also characterized in that the guide groove has different groove widths, wherein a first portion is designed as a groove channel with a constant groove width A, and wherein the groove width, after the groove channel, successively increases through a groove width B to a groove width C, and wherein, after the groove width C is reached, the groove width successively decreases through a groove width D to a groove width E.

The respiratory mask is alternatively also characterized in that the front groove edge and the rear groove edge extend away from each other between the groove width B and the groove width C.

The respiratory mask is alternatively also characterized in that the front groove edge and the rear groove edge extend toward each other between the groove width C and the groove width E.

The respiratory mask is alternatively also characterized in that, in the region of the groove width C, the rear groove edge is at a maximum distance from the plane of symmetry, and the front groove edge is arranged at a maximum proximity to the plane of symmetry.

The respiratory mask is alternatively also characterized in that the rear groove edge, in a region between the groove widths B and D, retreats in an arc shape, in such a way that the guide groove in this region is designed as a groove bay which comprises the end region.

The respiratory mask is alternatively also characterized in that the end region is arranged at a maximum distance from the plane of symmetry.

The respiratory mask is alternatively also characterized in that the groove bay is enclosed by the rear groove edge, wherein a groove bay width W successively decreases in the horizontal extent as the distance from the plane of symmetry increases.

The respiratory mask is alternatively also characterized in that the groove bay comprises a first groove bay width, a second groove bay width and a third groove bay width, which are formed by the horizontal extent of the rear groove edge, wherein the first groove bay width is greater than the second groove bay width, and wherein the second groove bay width is greater than the third groove bay width.

The respiratory mask is alternatively also characterized in that the first groove bay width is formed by the horizontal extent of the rear groove edge between the groove width B and the groove width D.

The respiratory mask is alternatively also characterized in that the second groove bay width is formed between two front web extensions.

The respiratory mask is alternatively also characterized in that the third groove bay width is formed between an upper central web extension and a lower central web extension.

The respiratory mask is alternatively also characterized in that the end region is arranged in the groove bay between the second groove bay width and the third groove bay width.

The respiratory mask is alternatively also characterized in that the height of the rear groove edge can increase in the region of the end region.

The respiratory mask is alternatively also characterized in that the end region of the guide groove is arranged spatially adjacent to the receiving element, wherein the receiving element spans the end region of the guide groove.

The respiratory mask is alternatively also characterized in that the receiving element spans the end region of the guide groove in such a way that a receiving space is formed.

The respiratory mask is alternatively also characterized in that the receiving element is an integral component of the outer side and of the groove edges.

The respiratory mask is alternatively also characterized in that the receiving element is an integral component of the outer side and of the rear groove edge.

The respiratory mask is alternatively also characterized in that the face part is produced from a rigid plastic selected from the group of the polyamides, polycarbonates, polyoxymethylenes, polysulfones and polypropylenes.

The respiratory mask is alternatively also characterized in that the face part is produced from polyamide PA12.

The respiratory mask is alternatively also characterized in that the receiving element is produced from the same material as the face part.

The respiratory mask is alternatively also characterized in that receiving element, outer side and rear groove edge are formed in one piece.

The respiratory mask is alternatively also characterized in that the receiving element comprises two webs, a bridge, a receiving diameter and a receiving opening.

The respiratory mask is alternatively also characterized in that the webs are connected to the rear groove edge via web extension surfaces, which comprise the front web extension and a rear web extension, wherein the webs are arranged spatially separate from the groove bottom.

The respiratory mask is alternatively also characterized in that the webs have a straight and/or curved design.

The respiratory mask is alternatively also characterized in that the webs are arranged at an angle $\varepsilon$ to the groove bottom, wherein the value of the angle $\varepsilon$ is in a range from 30° to 90°, preferably in a range from 30° to 60°.

The respiratory mask is alternatively also characterized in that the bridge is produced in one piece with the webs, wherein the bridge is arranged spatially separate from the groove bottom.

The respiratory mask is alternatively also characterized in that the webs, the bridge and the groove bottom delimit the receiving space.

The respiratory mask is alternatively also characterized in that the bridge is at least in part circular with a receiving diameter, and wherein the bridge is interrupted by a receiving opening.

The respiratory mask is alternatively also characterized in that the bridge is of semicircular shape.

The respiratory mask is alternatively also characterized in that the receiving element comprises at least one central web and at least one, preferably two apertures, wherein the central web is arranged between the bridge and the outer side.

The respiratory mask is alternatively also characterized in that the central web is arranged at the halfway point of the bridge.

The respiratory mask is alternatively also characterized in that the at least one central web is connected to the rear groove edge via a central web extension surface, which comprises the upper central web extension and the lower central web extension, wherein the central web is arranged spatially separate from the groove bottom.

The respiratory mask is alternatively also characterized in that the receiving opening is smaller than the receiving diameter.

The respiratory mask is alternatively also characterized in that the receiving opening is oriented to the front.

The respiratory mask is alternatively also characterized in that the connection element is a releasable part of the respiratory mask.

The respiratory mask is alternatively also characterized in that the connection element is produced from the same material as the face part.

The respiratory mask is alternatively also characterized in that the connection element comprises a fastening element and a holding web, wherein the fastening element and the holding web are arranged on mutually opposite sides of the connection element.

The respiratory mask is alternatively also characterized in that a base surface of the connection element has a cutout which extends from the inner base surface to the outer base surface, as a result of which the holding web is formed.

The respiratory mask is alternatively also characterized in that the cutout has a crescent shape.

The respiratory mask is alternatively also characterized in that the holding web is configured to receive a harness, wherein the harness is configured to fasten the respiratory mask to the head of a user and/or patient.

The respiratory mask is alternative also characterized in that the fastening element comprises a button plate, an overhang and a neck, wherein the button plate is integrally formed on the connection element via the neck.

The respiratory mask is alternatively also characterized in that the button plate and the neck are round or rounded and each have a maximum diameter, wherein the maximum diameter of the button plate is greater than the maximum diameter of the neck.

The respiratory mask is alternatively also characterized in that the receiving element is configured and designed to releasably receive the connection element via the fastening element integrally formed on the connection element.

The respiratory mask is alternatively also characterized in that the receiving opening is configured and designed to receive the neck and guide it into the receiving diameter.

The respiratory mask is alternatively also characterized in that the receiving space is configured and designed to receive the button plate.

The respiratory mask is alternatively also characterized in that the connection element is connected reversibly to the receiving element by reception of the fastening element in the receiving diameter and the receiving space.

The respiratory mask is alternatively also characterized in that the connection of the connection element to the receiving element is movable, in particular rotationally movable.

The respiratory mask is alternatively also characterized in that the connection element comprises a side wall, wherein the side wall comprises at least one, preferably two grip recesses, which are wider than the side wall.

The respiratory mask is alternatively also characterized in that the at least one grip recess comprises a grip recess inner wall and a grip recess outer wall, wherein the grip recess outer wall comprises at least one structural element designed in the form of ribs, corrugations, lattice structures, meshes and/or dots, for example in the form of rib-like elevations.

BRIEF DESCRIPTION OF THE DRAWINGS

Exemplary embodiments of the respiratory mask according to the invention are shown in the figures. Shown are:

FIG. 1: a respiratory mask 100 laterally from the front.

DETAILED DESCRIPTION OF EXEMPLARY EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawings making apparent to those of skill in the art how the several forms of the present invention may be embodied in practice.

The respiratory mask 100 according to the invention can be a mask for ventilation, a mask for respiratory assistance or a protective mask. The respiratory mask 100 can be a protective mouth-and-nose mask, a nose mask or a full-face mask. The mask in the following exemplary embodiments is a full-face mask for ventilation.

Figure 1:
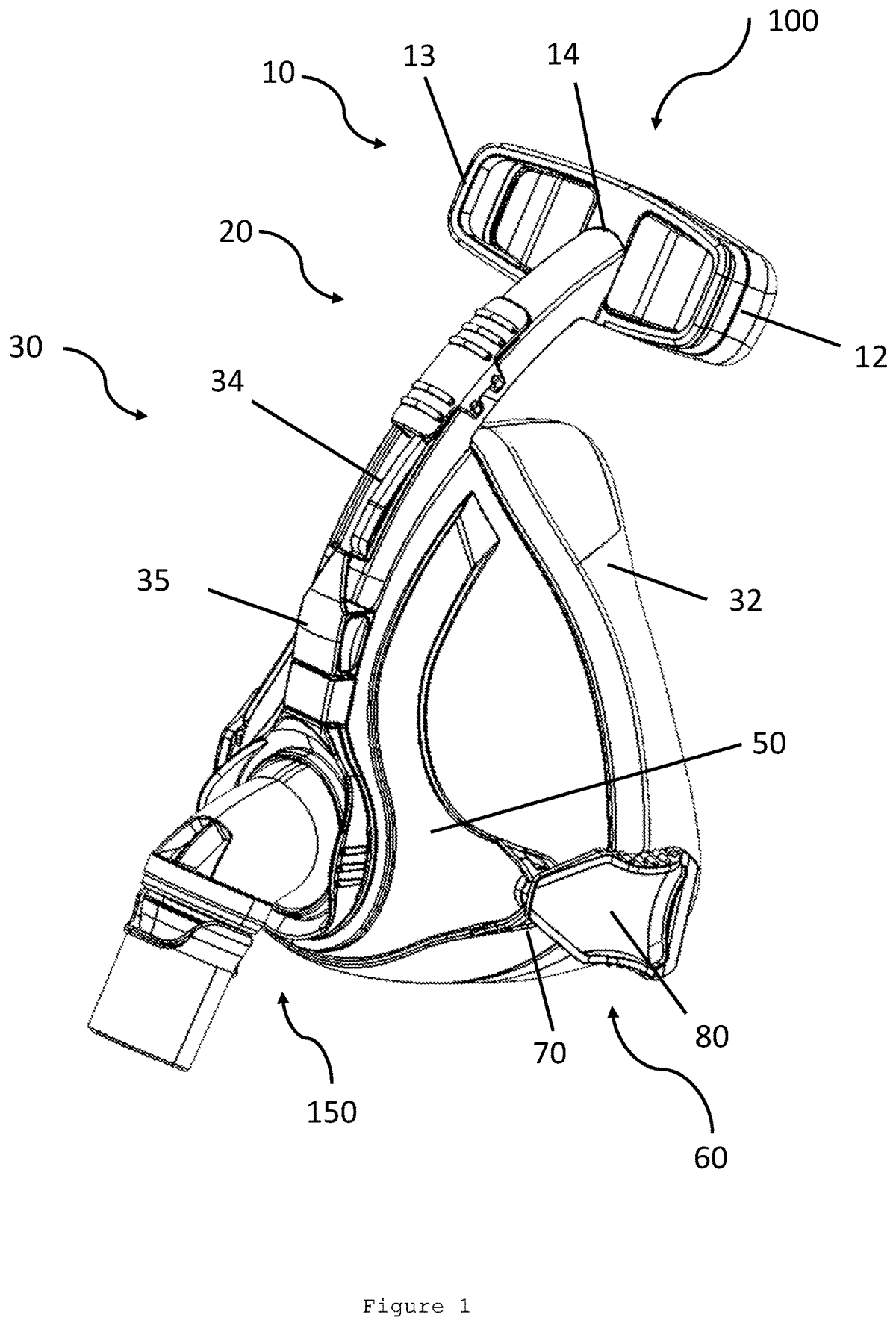
Figure 2:
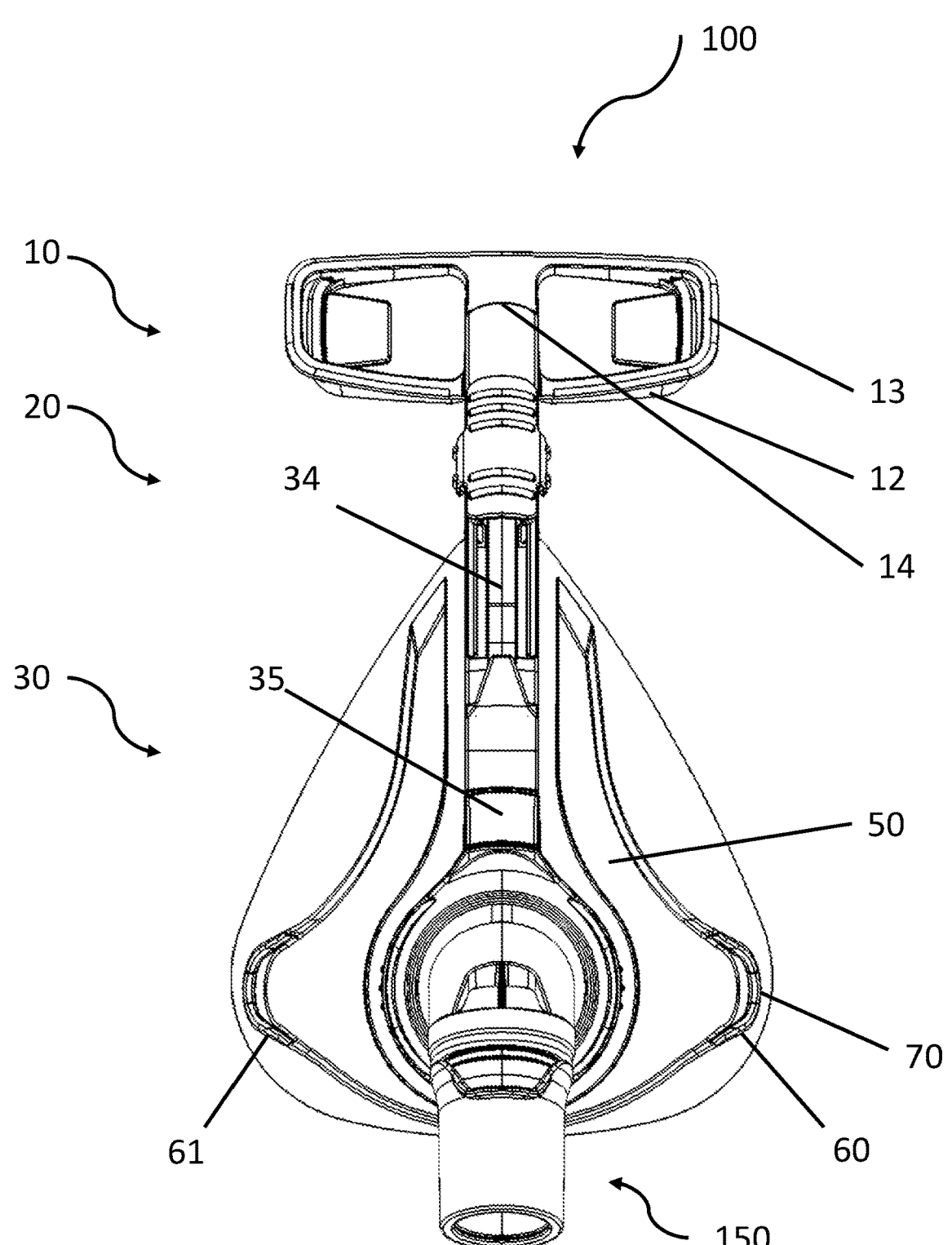
FIG. 2: a respiratory mask without connection element 80, in a plan view from the front.
Figure 3:
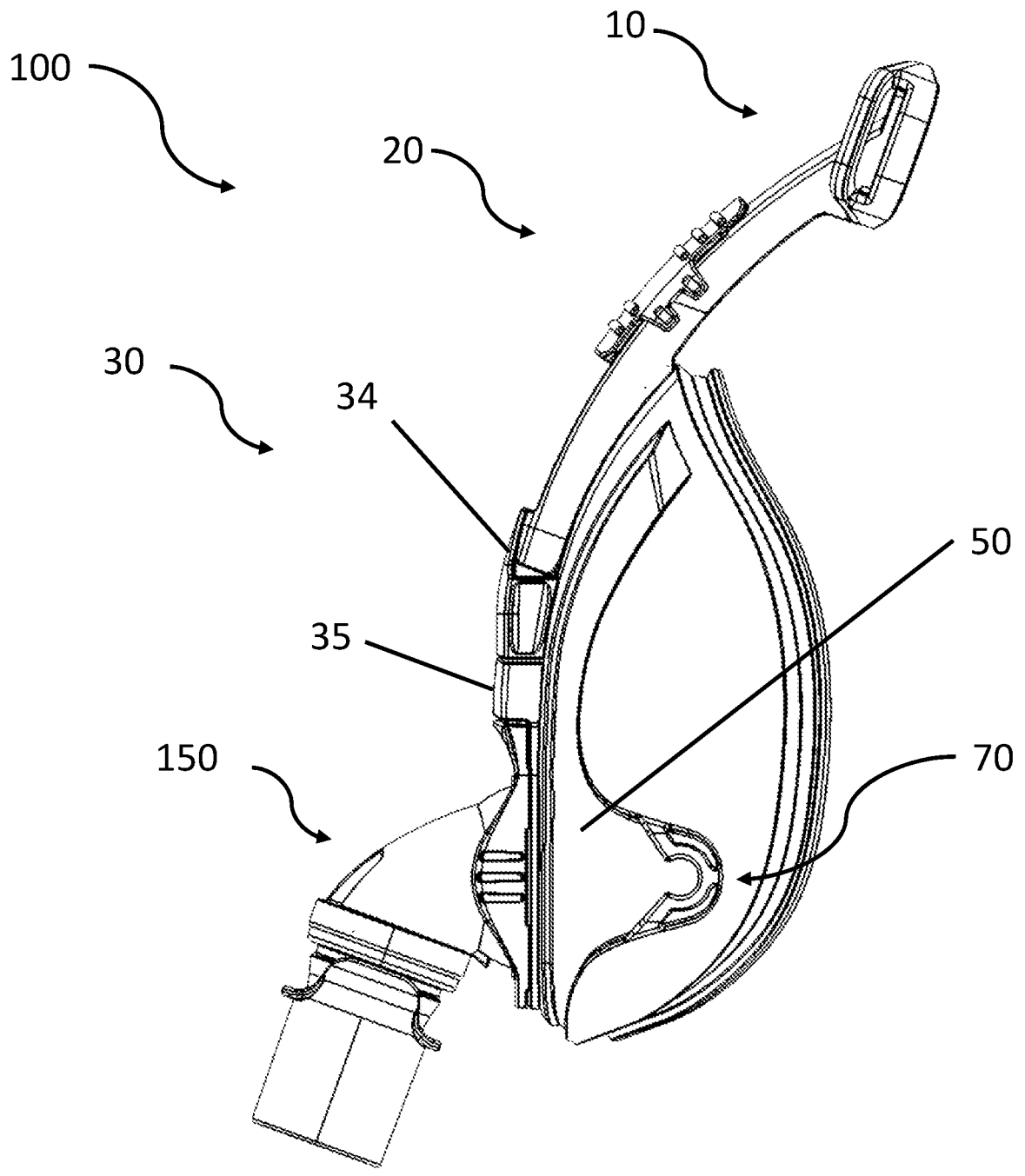
FIG. 3: a respiratory mask without connection element, from the left.

FIG. 1 to FIG. 3 show, from different perspectives, a respiratory mask for breathing and/or ventilation, with a forehead part 10, a transition part 20 and a face part 30 and also a hose attachment system 150.

The forehead part 10 comprises a forehead cushion 12, at least one upper anchor point 13 and a connection site 14 (see FIGS. 1 and 2).

The transition part 20 can connect the forehead part 10 to the face part 30 via the connection site 14. The transition part 20 can be mounted so as to be longitudinally adjustable and movable.

The face part 30 can comprise a circumferential seal 32 (only shown in FIG. 1), a coupling site 34, an intermediate member 35, an outlet 36 (not shown), a guide region 50 and at least two anchor points 60/61. The at least two anchor points 60/61 each comprise a receiving element 70 and a connection element 80 (only shown in FIG. 1).

Figure 4:
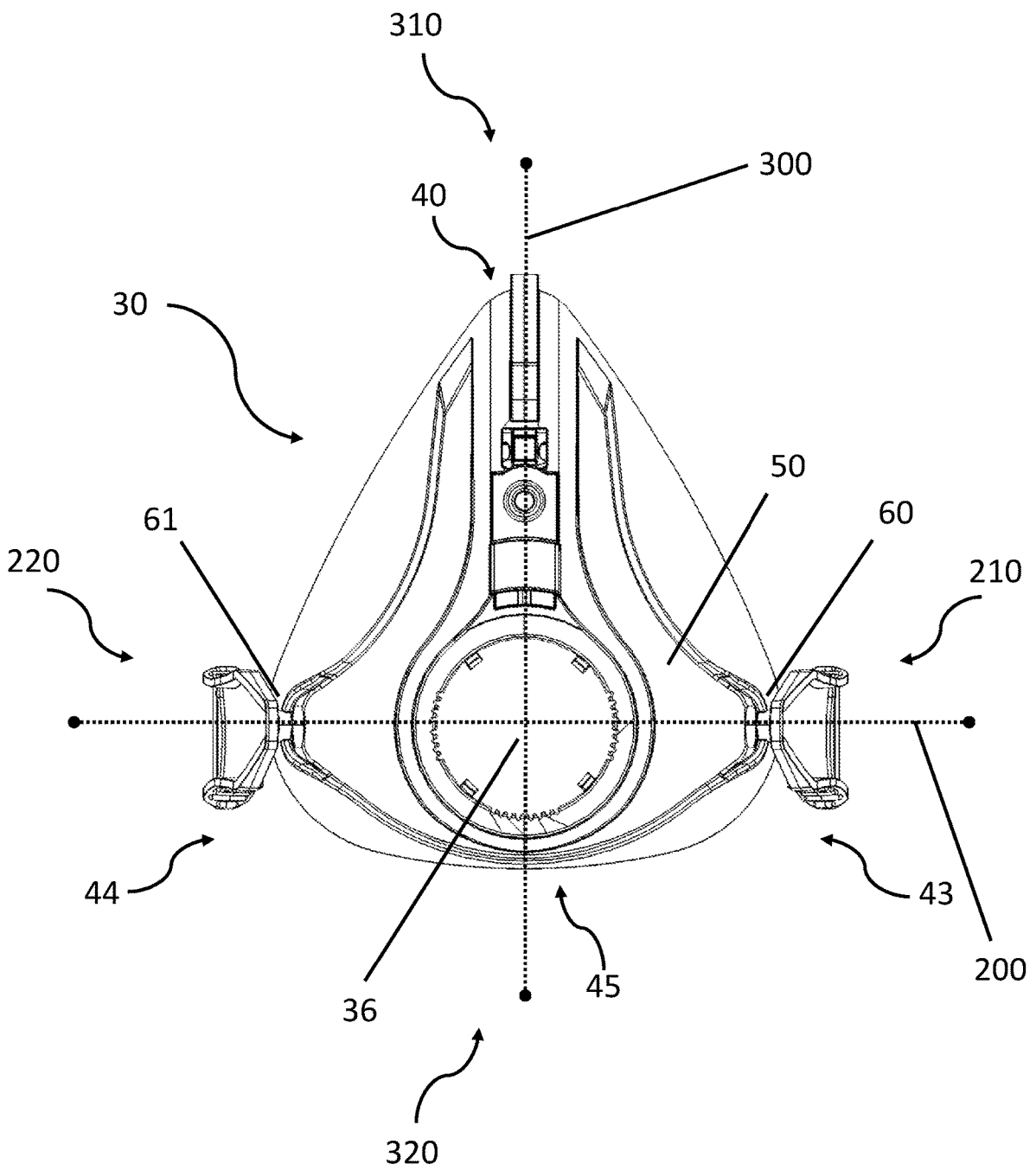
FIG. 4: a face part from the front, in order to illustrate the directions and positional relationships used herein.

FIG. 4 shows a face part 30 in a plan view from the front 520. The face part 30 has the customary design of an approximate triangular shape. The triangular shape of the face part 30 preferably has rounded corners or tips. The triangular shape preferably has no straight lines and is instead designed curving slightly outward.

A tip 40 of the triangle is defined as the upper end or as lying at the top 310. The tip 40 of the triangle is arranged at a 12 o'clock position and is configured to bear on the bridge of the nose. The two other corner points of the triangle are defined as lower corner points 43/44.

A base 45 of the triangle connects the two lower corner points 43/44 and is defined as the lower end or as lying at the bottom 320. The base 45 of the triangle is deigned to bear on the region between lower lip and chin.

The lower corner points 43/44 are arranged at a 3 o'clock position and a 9 o'clock position, if an outlet 36 described below is regarded as the center point of an imaginary clock face. The corner point arranged at a 3 o'clock position, when considering the outer side 31, is defined as the bottom left corner point 43. The corner point arranged at a 9 o'clock position, when considering the outer side 31, is defined as the bottom right corner point 44.

For better clarity, a horizontal plane 200 and a vertically extending plane of symmetry 300 are defined herein. The horizontal plane 200 runs horizontally. The horizontal plane 200 defines the maximum width of the face part 30.

The maximum width of the face part 30 lies in a range from 80 mm to 120 mm, preferably from 95 mm to 100 mm. For example, the maximum width of the face part 30 is 98 mm. The two anchor points 60/61 are arranged in the region of the maximum width of the face part.

The plane of symmetry 300 lies perpendicular to the horizontal plane 200. In this exemplary embodiment, the face part 30 has mirror symmetry, which means that the face part 30 can be mirrored via the plane of symmetry 300 shown herein.

The terms plane of symmetry 300 and horizontal plane 200 here retain their validity even when the respiratory mask 100 is shown inclined or rotated and the planes appear different. The plane of symmetry 300 defines the maximum length of the face part 30.

The maximum length of the face part 30 lies in a range from 40 mm to 200 mm, preferably in a range from 80 mm to 140 mm, particularly preferably in a range from 90 mm to 130 mm. For example, the face part can be designed in three size categories, wherein the maximum length of the face part 30 in a small format is for example in the range from 90 mm to 105 mm, in a medium format for example in a range from 105 mm to 116 mm, and in a large format for example in a range from 116 mm to 130 mm.

In the case of a predetermined maximum mask width of 98 mm, the ratio of the maximum width to the maximum length of the face part 30 lies in a small format for example in a range from 1:0.9 to 1:1.07, in a medium-sized format for example in a range from 1:1.07 to 1:1.18, and in a large format for example in a range from 1:1.18 to 1:1.33.

Figure 5:
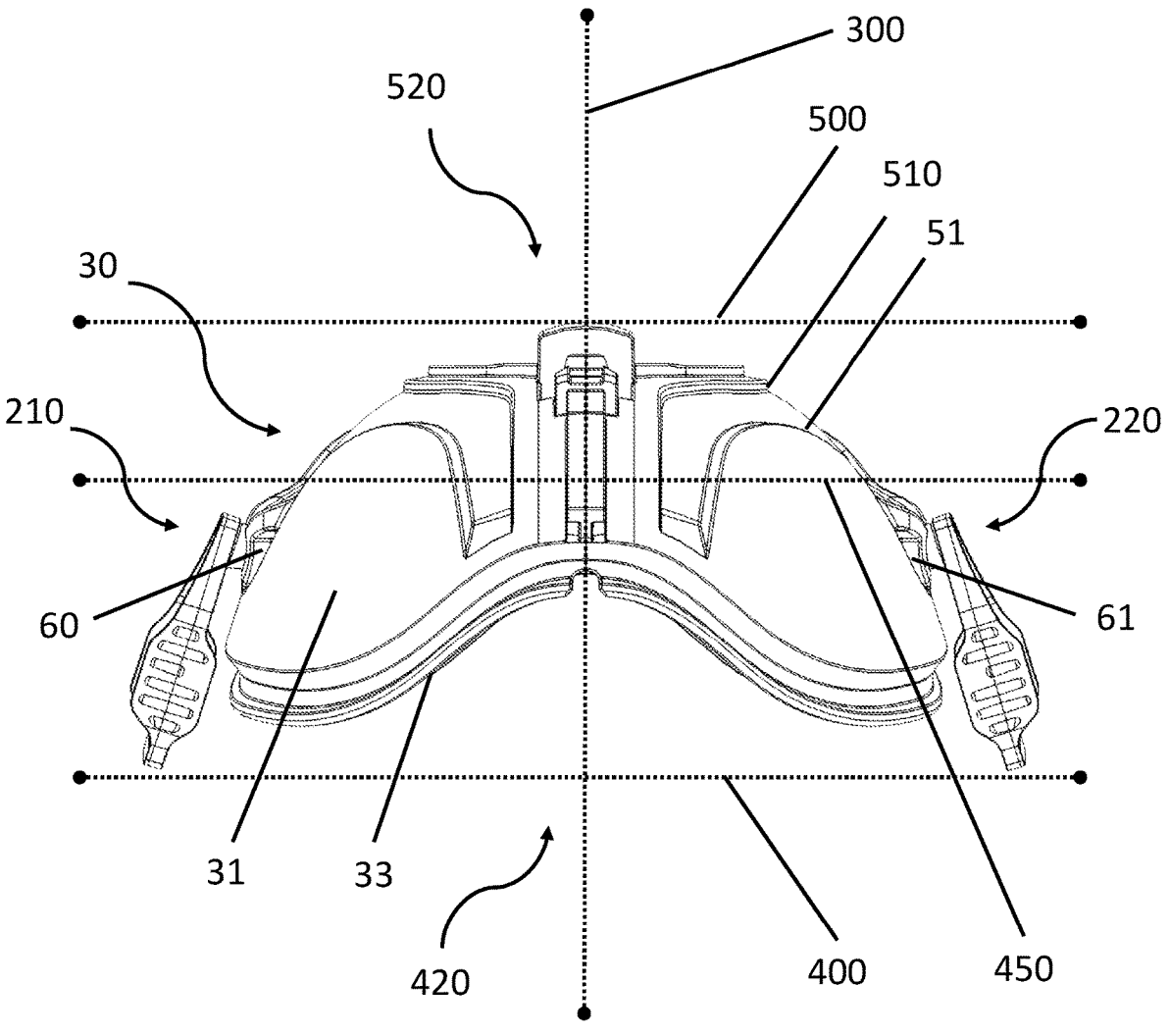
FIG. 5: a face part from above.
Figure 6:
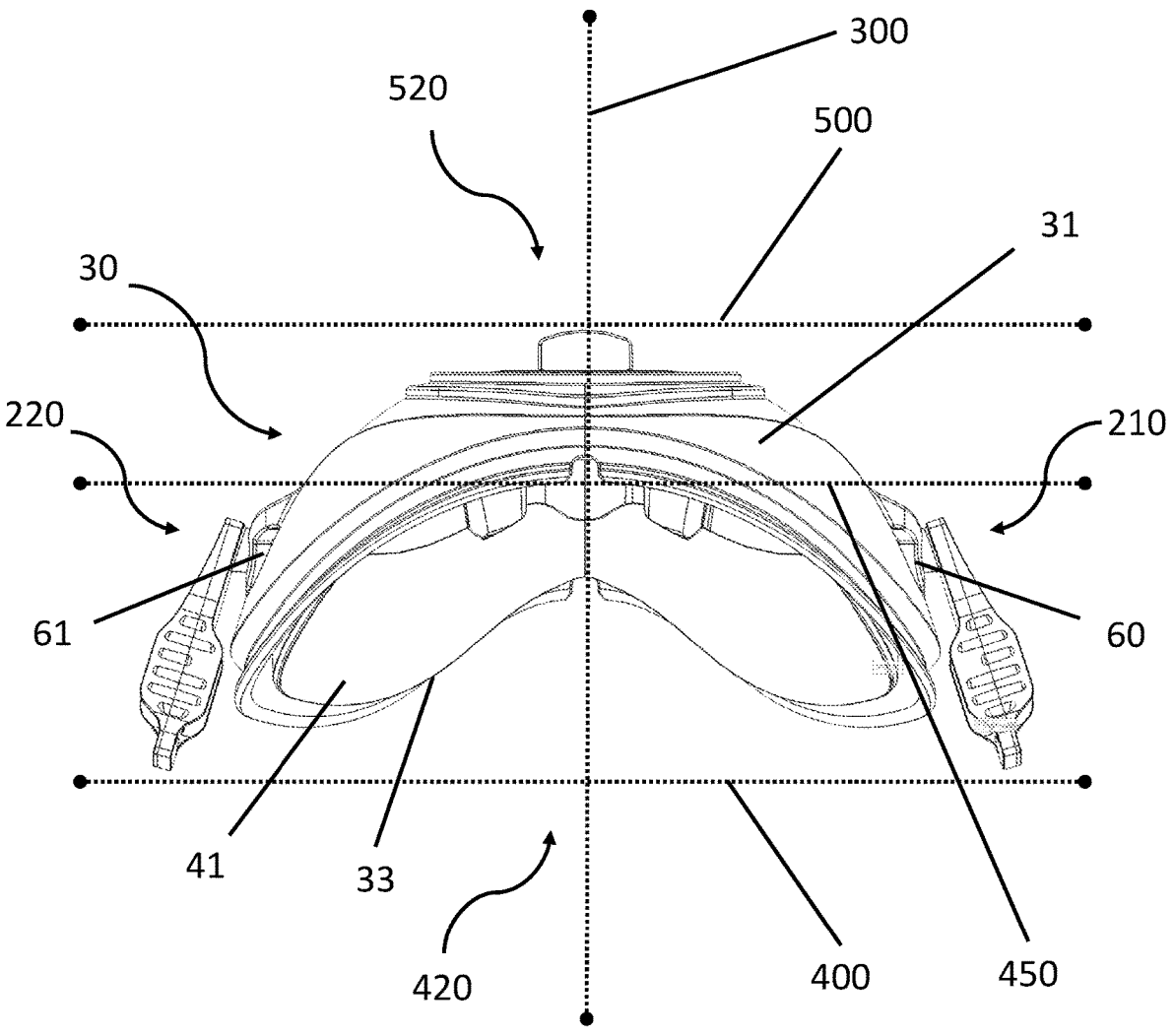
FIG. 6: a face part from below.

FIG. 5 shows a face part 30 seen from above 310, and FIG. 6 shows a face part 30 shown from below 320. A front plane 500, a central plane 450 and a rear plane 400 are sections of the horizontal plane 200 (FIG. 4). The plane of symmetry 300 is perpendicular to the planes 500/400/300.

In a state of use, the front plane 500 is directed away from a face of the patient (not shown). In a state of use, the rear plane 400 corresponds to the plane of the face of the patient (not shown). The distance between the planes 400 and 500 defines the maximum depth of the face part 30.

An outer side 31 of the face part 30 is by definition the side which, in a state of use, is directed away from the face of the patient (not shown). The outer side 31 faces toward the front plane 500 and accordingly lies to the front 520.

An inner side 41 of the face part 30 is by definition the side which, in a state of use, is directed toward the face of the patient (not shown). The inner side 41 (only shown in FIG. 6) faces toward the rear plane 400 and accordingly lies to the rear 420.

The face part 30 is produced from a plastic, for example. The face part 30 can be produced by an injection molding method, for example. However, other suitable materials and production methods are also conceivable which appear to be suitable in terms of stability, strength, flexibility, temperature resistance, weight, cost, biocompatibility, appearance and comfort.

The face part 30 is preferably produced from a rigid plastic. Suitable plastics comprise, for example, polyamides, polycarbonates, polyoxymethylenes, polysulfones and polypropylenes. For example, the face part 30 is produced from polyamide PA12. The advantages of polyamide PA12 lie in its very good temperature resistance, a high load-bearing capacity and a high degree of transparency of the material.

In the present exemplary embodiment, the material of the face part 30 is a gas-impermeable material. However, it is also conceivable that the face part 30 is made of a gas-permeable material.

It is clear from FIG. 5 and FIG. 6 that the outer side 31 of the face part 30 has a largely convex curvature, and the inner side 41 (see FIG. 6) of the face part 30 has a largely concave curvature. On account of the curvature of the face part 30, the outer edge 33 points to the rear 402, and a cavity forms between the surface of a face (not shown) and the face part 30 of the respiratory mask 100. In a state of use, respiratory gas is located in this cavity. The cavity is preferably of such a size that the inner side 41 of the face part 30 does not touch the surface of the face. At the same time, the cavity is preferably as small as possible, so that the region in which the respiratory gas is located is as small as possible. A volume that is as small is possible is advantageous, since the volume in which mixed gas or $CO_2$ can collect is then kept as small as possible.

It is clear from FIG. 4 that the anchor points 60/61 are arranged in the region of the maximum width of the face part. It is moreover clear from FIGS. 5 and 6 that the anchor points 60/61 in this exemplary embodiment are arranged in a region between the central plane 450 and the rear plane 400.

The anchor points 60/61 advantageously lie as far below 320 as possible and as far to the rear 420 as possible, which increases the stability of the respiratory mask 100 after it has been placed on the face. The anchor points 60/61 thus lie as close as possible to the face (not shown) of a patient. However, after the mask has been placed on the face, the anchor points 60/61 lie so far away from a face (not shown) that a connection element 80 (described hereinbelow) cannot touch the face.

Figure 7:
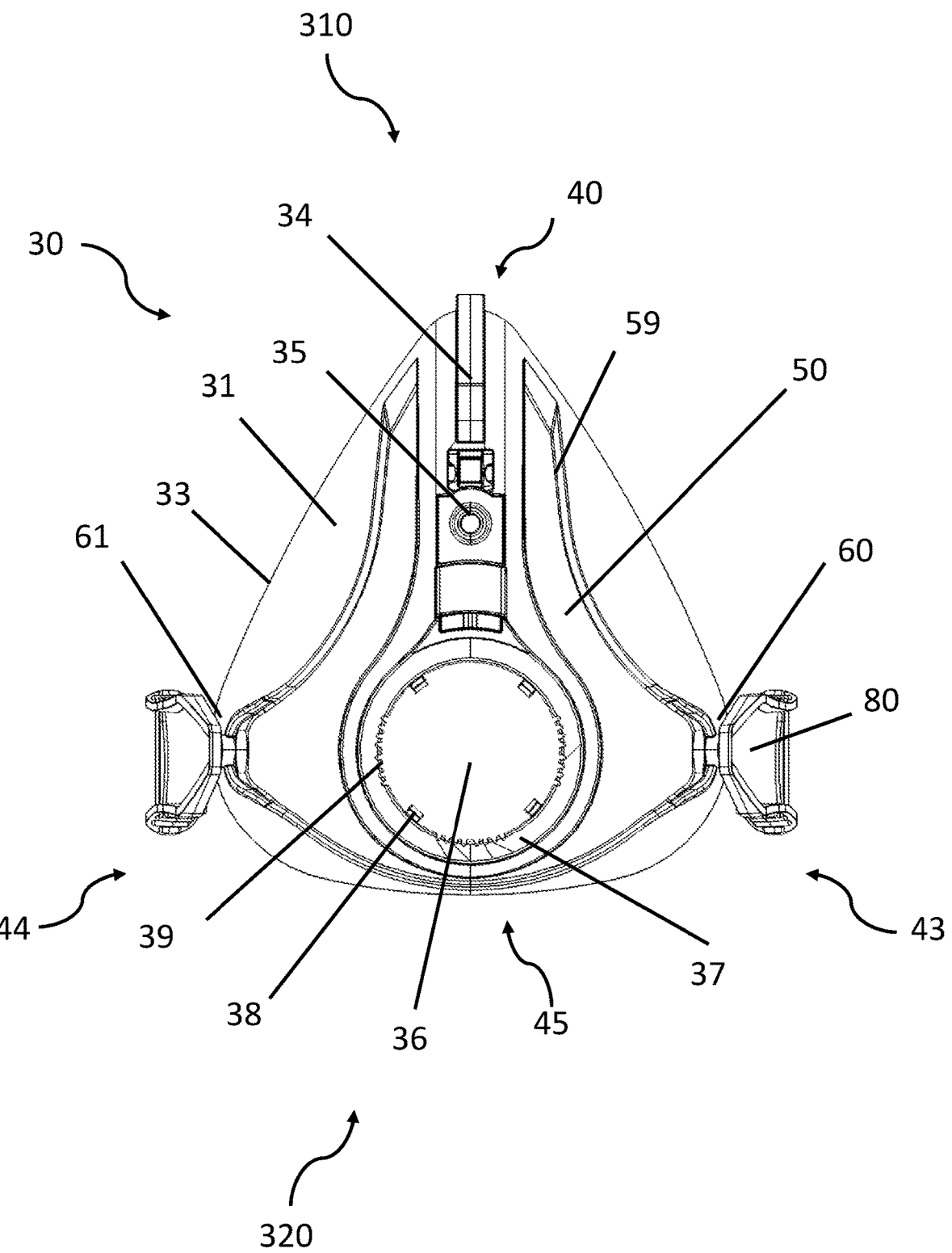
FIG. 7: a face part in a plan view from the front.

FIG. 7 shows the face part 30 in a plan view from the front 520. The face part 30 comprises, as described above, an outer side 31 and an inner side 41 (not shown here). The face part 30 is delimited by an outer edge 33. The outer edge 33 is configured to receive a seal 32 (described below).

The face part 30 usually has a seal 32 (see FIG. 1) which is arranged at the outer edge 33 of the face part 30. The seal 32 is arranged continuously on the entire outer edge 33 of the face part 30. The circumferential seal 32 is configured to bear on the skin of the face of a user/patient. The circumferential seal 32 is configured to be flexible, in order to conform to the face of the user/patient. The circumferential seal 32 is preferably produced from a flexible plastic, for example from a silicone. However, other suitable materials are also conceivable which appear to be suitable in terms of gas sealing, stability, flexibility and comfort.

In this exemplary embodiment, the face part 30 has a gas-tight design relative to the ambient air. In this exemplary embodiment, a gas exchange can take place only via the outlet 36 described below.

A coupling site 34 can be arranged at the tip 40 of the face part 30. By way of the coupling site 34, the face part 30 can be connected to a forehead part 10 via a transition part 20. The coupling site 34 can connect the face part 30 to the transition part 20. The coupling site 34 can protrude beyond the outer surface of the face part 30 and form a projection. A transition part 20 can be attached to this protruding projection. The coupling site 34 can be configured as a guide rail, for example.

The coupling site 34 can be designed in one part or in two parts. The coupling site 34 is preferably formed integrally with the face part 30 and made of the same material as the face part 30. In other words, the coupling site 34 is a fixed component of the face part 30. However, it is also conceivable that face part 30 and coupling site 34 are formed in two parts. In a two-part design, face part 30 and coupling site 34 can be produced from the same material. However, it is also conceivable that the coupling site 34 is made from a different material than the face part 30.

An intermediate member 35 can be arranged adjacent to the coupling site 34 from below 320. In other words, an intermediate member 35 can be arranged between the coupling site 34 and an outlet 36 (described below). Further functional elements can be arranged in the intermediate member 35, in particular measurement nozzles, for example a pressure measurement nozzle or a $CO_2$ measurement nozzle or the like (not shown).

An outlet 36, for example with a round shape, can be arranged under the intermediate member 35 and between the lower corner points 43/44 of the face part 30. The outlet 36 can also have any other shape, from round to oval to polygonal. In the case of a protective mask, the outlet can also be made of a gas-permeable material over a large area. The outlet 36 can be designed as an opening or be closed.

The outlet 36 shown in FIG. 7 is designed as a circular opening in the face part 30. The outlet 36 comprises an outlet edge 37, which can have one or more notch elements 39 and latching elements 38. By way of these elements, further attachment units can be introduced into the opening, for example an attachment nozzle for receiving a connection hose with which the face part 30 can be connected to a respiratory gas source. A hose attachment system 150 (see FIG. 1-3) can thus be attached to the outlet 36.

In other embodiments, it is also conceivable that the outlet 36 is closed. For example, the outlet 36 can be produced from another material than the face part 30. It is conceivable that the outlet 36 is produced from a material which permits a gas exchange, whereas the face part 30 is produced from a material which does not permit a gas exchange.

The face part 30 moreover comprises, as described below, at least one guide region 50 and the at least two anchor points 60/61, each with a receiving element 70 and a connection element 80. The guide region 50 is configured for guiding a connection element 80 to a receiving element 70 and, for example, is designed as a guide groove 50.

Figure 8:
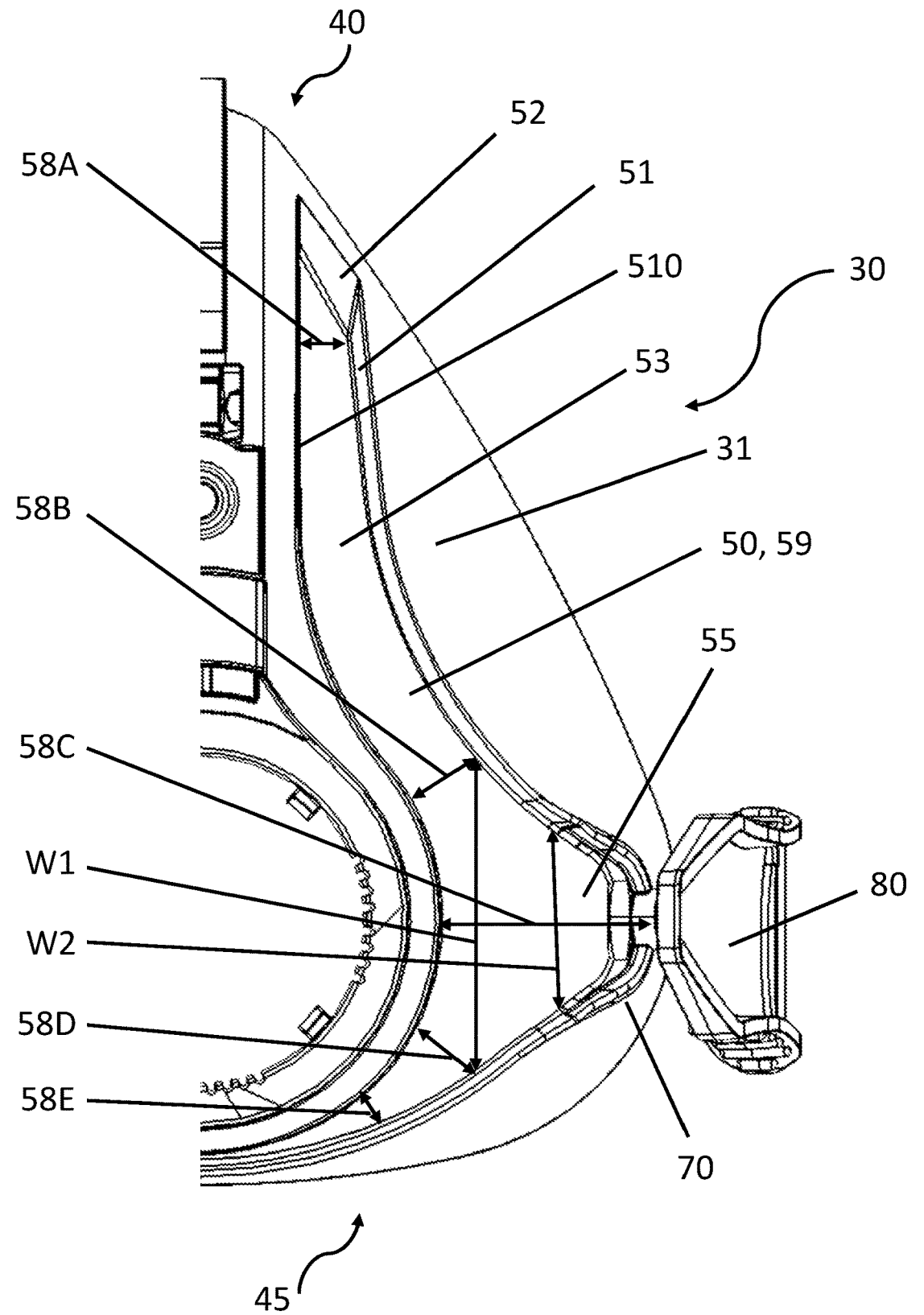
FIG. 8: a detail of the face part in a plan view from the front.
Figure 9:
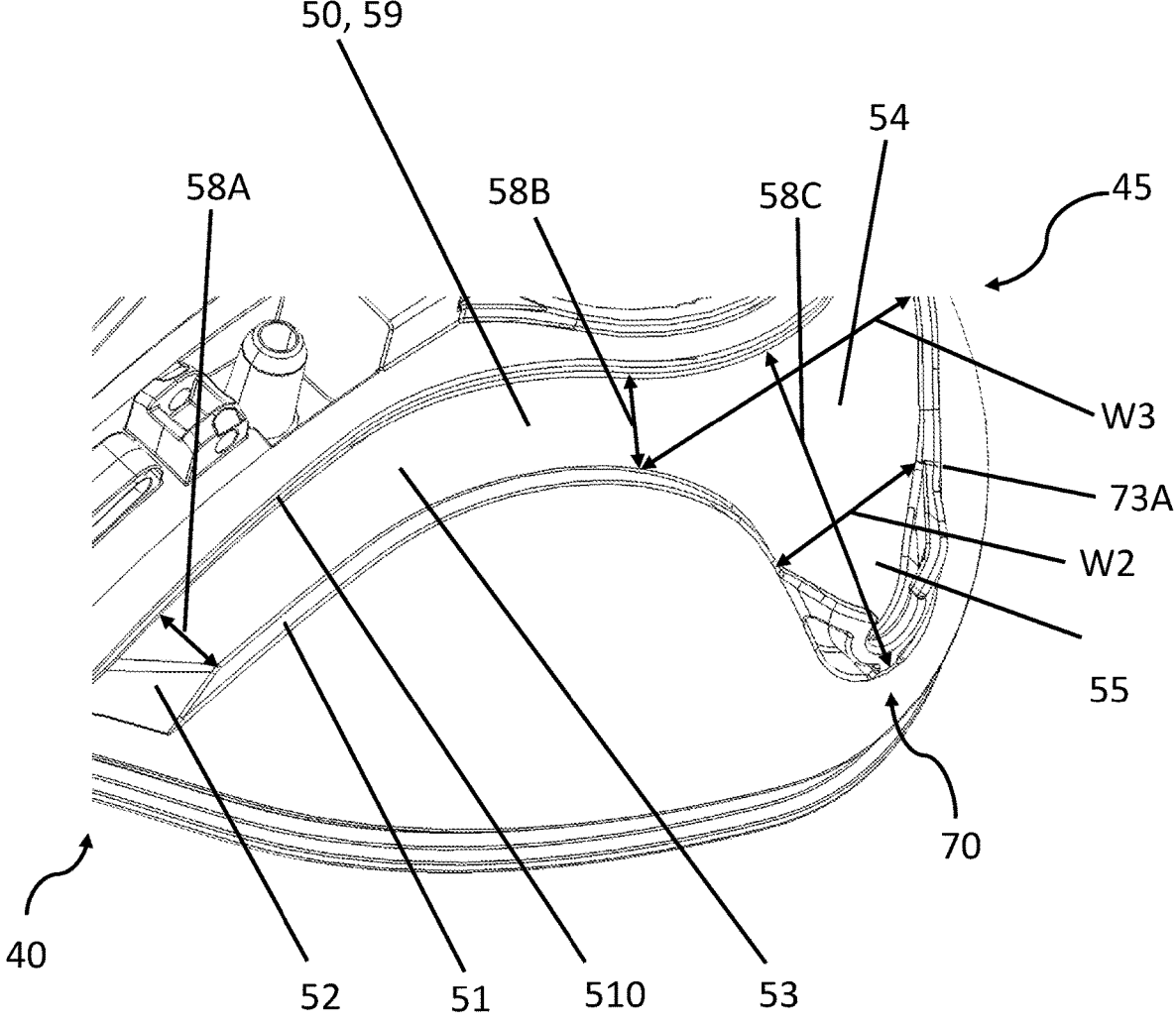
FIG. 9: a perspective view of a detail of the face part obliquely from above.

FIG. 8 shows a detail of the face part 30, in a plan view from the front 520, with the outer side 31 of the face part 30, which comprises at least one guide groove 50. FIG. 9 shows a perspective view of a detail of the face part 30 obliquely from above 310.

The guide groove 50 allows the user and/or the patient to guide a connection element 80 (described below) along the guide groove 50. It is envisioned in particular to guide a connection element 80 to a receiving element 70 (explained below) which is arranged spatially adjacent to an end region 55 (see below) of the guide groove 50.

The guide groove 50 can be formed, for example, by a depression 59 in the outer side 31 of the face part 30. It is also conceivable that the guide groove 50 is formed by elevations on the outer side 31 of the face part, for example by raised guide borders or the like.

The guide groove 50 is arranged on at least one side of the face part 30, preferably on both sides. Particularly preferably, the guide groove 50 is formed symmetrically with respect to both sides of the plane of symmetry 300 (FIG. 4).

FIG. 8 and FIG. 9 show an exemplary embodiment of the face part 30 with a guide groove 50 which is designed as a depression 59 in the outer side 31. The guide groove 50 in this exemplary embodiment is axially symmetrical over the plane of symmetry 300. To make matters simpler, only one of the symmetrical halves of the guide groove 50 is described below.

The depression 59 of the guide groove 50 lies in a range from 0.5 mm to 6 mm, preferably from 0.8 mm to 2 mm; for example, the guide groove 50 has a depth of substantially 1 mm. At specially designed regions of the guide groove 50, the depression 59 can have in part a depth that deviates from the rest of the guide groove 50. The degree of the depression 59 is thus chosen in such a way that the guide groove 50 affords safe and simple handling for the user and/or the patient.

The guide groove 50 can be straight and/or curved. The guide groove 50 can extend over the entire face part 30 or only over parts of the face part 30. The guide groove 50 extends over 5% to 100% of the length of the face part 30, preferably over 50% to 100%, for example over 95% of the length of the face part 30.

In the exemplary embodiment shown, the at least one guide groove 50 extends over almost the entire outer side 31 and is arranged running largely vertically from the tip 40 to the base 45.

The guide groove 50 begins at a groove inlet 52. In this exemplary embodiment, the groove inlet 52 lies at the tip 40 of the face part 30. It is also conceivable that the groove inlet 52 lies at another point of the face part 30, for example at the base 45.

The groove inlet 52 forms, through a successive depression, a transition from the outer side 31 of the face part 30 to the final depression 59 of the guide groove 50.

In the present exemplary embodiment, the depression 59 is of substantially constant depth after the groove inlet. The depression 59 can also have varying depths. For example, the depression 59 of the guide groove 50 can be deeper at an end region 55 (described in more detail below) of the guide groove 50.

The guide groove 50 comprises a rear groove edge 51 and a front groove edge 510. The rear groove edge 51 is the groove edge which lies substantially closer to the rear plane 400, and the front groove edge 510 is the groove edge which lies substantially closer to the front plane 500 (see also FIG. 5).

In the present exemplary embodiment, the rear groove edge 51 and the front groove edge 510 have no point of contact. In other embodiments, it is conceivable that the front groove edge 510 and the rear groove edge 51 connect at one or more locations, particularly when the outer side 31 of the face part 30 comprises two or more guide grooves 50.

In the present exemplary embodiment, the groove edges 51, 510 are continuous and have no interruptions.

In the present exemplary embodiment, the groove edges 51, 510 have an almost smooth surface. It is also conceivable that one of the groove edges 51, 510 and/or both groove edges 51, 510 has/have a structure, for example a ribbing.

A structure of the groove edges 51, 510 could improve the guiding property, since the ribbing gives the user tactile feedback as regards the guiding in the guide groove 50. For example, the ribbing can also be another regularly or irregularly formed structure. The structure can be formed in the groove edges 51, 510 in such a way that the user, who guides a connection element 80 along a groove edge 51, 510 of the guide groove 50, receives tactile feedback regarding the approach to the receiving element 70. In this example, the structure of the groove edge 51, 510 would be arranged such that the structure in the regions of the groove edge 51, 510 closer to the receiving element 70 is increasingly or decreasingly more regular or more irregular.

The guide groove has a groove width 58. The groove width 58 of the guide groove 50 is substantially dependent on the position of the rear groove edge 51 to the front groove edge 510. The groove width 58 of the guide groove 50 can be constant or can vary.

The groove width 58 of the guide groove 50 at the groove inlet 52 is 6 mm to 12 mm, preferably 8 mm to 12 mm, for example 10 mm. The groove width 58 directly after the groove inlet 52 is by definition groove width 58A.

A guide groove 50 with a constant groove width 58 which corresponds to the groove width 58A can extend directly from the groove inlet 52 to the end region 55 (see below) of the guide groove 50 arranged spatially adjacent to a receiving element 70.

In the exemplary embodiment shown in FIG. 8 and FIG. 9, the guide groove 50 has different groove widths 58. The guide groove 50 begins at the groove inlet 52 with a groove width 58A. The groove width 58A is constant in a first portion. A first portion of the guide groove 50 with a substantially constant groove width 58A is here designated as groove channel 53.

In a guide groove 50 with constant groove width 58, the rear groove edge 51 and the front groove edge 510 extend parallel to each other. A parallel course is also given in the case of a curved profile of the guide groove 50 with constant groove width 58, in which case the groove edges 51, 510 describe a parallel curve.

The groove channel 53 can extend by any desired length along the length of the face part 30. For example, the groove channel 53 extends over 50% of the length of the face part 30.

In the present exemplary embodiment, the groove width 58 of the guide groove 50 increases after the groove channel 53. The width of the guide groove 50 having a greater width than the groove width 58A is designated as groove width 58B. The groove channel 53 ends directly before the groove width 58B.

The guide groove 50 can be designed widening from the groove width 58B. For example, the groove width 58 can increase successively. After the groove channel 53, the guide groove widens from the groove width 58B as far as the maximum groove width 58C.

In the present exemplary embodiment, the groove width 58 of the guide groove decreases again after the groove width 58C. Groove width 58D corresponds to the groove width 58B. After the groove width 58D is reached, the guide groove 50 in the present exemplary embodiment extends along the base 45 and connects at the plane of symmetry 300 to that part of the guide groove 50 which, in identical or mirror image form, begins at the upper left end and runs to the base 45.

In the exemplary embodiment shown, the connection at the base 45 is less wide than in the upper part of the guide groove 50. At the base there is a groove width 58E, which has a smaller width than groove widths 58A or 58B and 58D.

The increase in the groove width 58 between groove width 58B and 58D is associated with the front groove edge 510 and the rear groove edge 51 extending away from each other. Starting from the groove width 58B, the front groove edge 510 runs substantially vertically along the outlet 36 and extends close to the plane of symmetry 300.

Starting from the groove width 58B, the rear groove edge 51 moves away from the plane of symmetry 300 and extends in the direction of the rear plane 400, such that the guide groove 50 widens in the horizontal plane 200. The groove width 58C is the widest location of the guide groove 50 in the horizontal direction. Starting from the groove width 58C, the rear groove edge 51 extends again in the direction of the plane of symmetry 300.

The horizontal course of the guide groove 50 between the groove width 58B and the groove width 58D is bay-shaped and is designated as groove bay 54. Bay-shaped signifies that, as a result an arc-shaped retreat of the rear groove edge 51, the guide groove 50 in this region has the shape of a bay or of an open arc. The groove bay 54 can, for example, have a round profile; a polygonal profile is also conceivable. The groove bay 54 is enclosed by the rear groove edge 51.

In the exemplary embodiment shown, the guide groove 50 ends in the horizontal plane 200 at an end region 55. The end region 55 is arranged, in the horizontal direction, at a maximum distance from the plane of symmetry 300 (FIG. 5).

The end region 55 lies on a plane with a groove bottom 56 (described further below) and lies spatially adjacent to a receiving element 70, which spans the guide groove 50 in this end region 55. In the present exemplary embodiment, the end region 55 is enclosed in a bay shape by the rear groove edge 51.

The end region 55 can be deeper than the rest of the guide groove 50. The depression 59 in the end region 55 is between 1 mm and 6 mm deep. For example, the depression 59 in the region of the end region is 4 mm deep.

Figure 10:
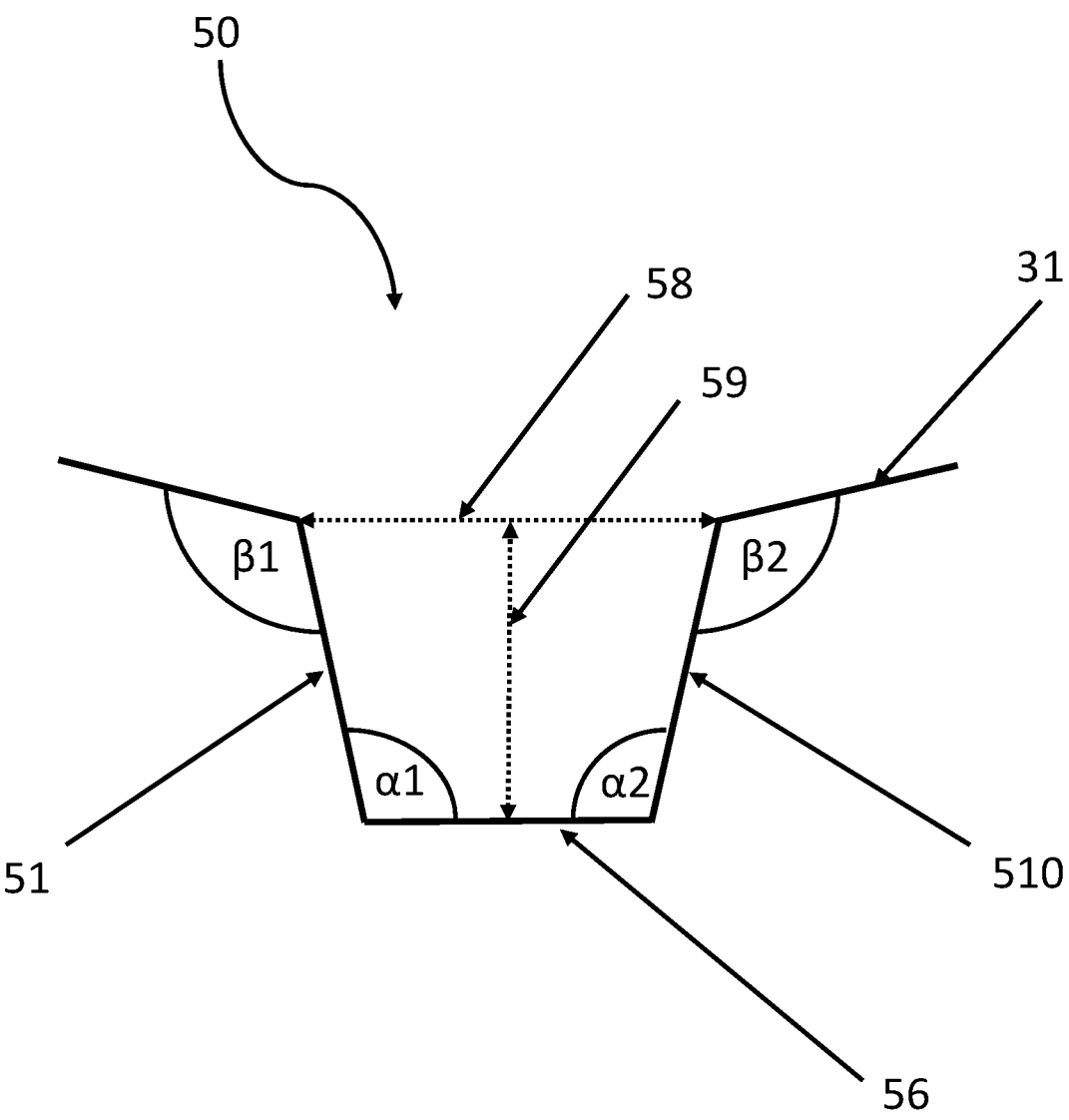
FIG. 10 and FIG. 11: schematic cross sections of a guide groove.
Figure 11:
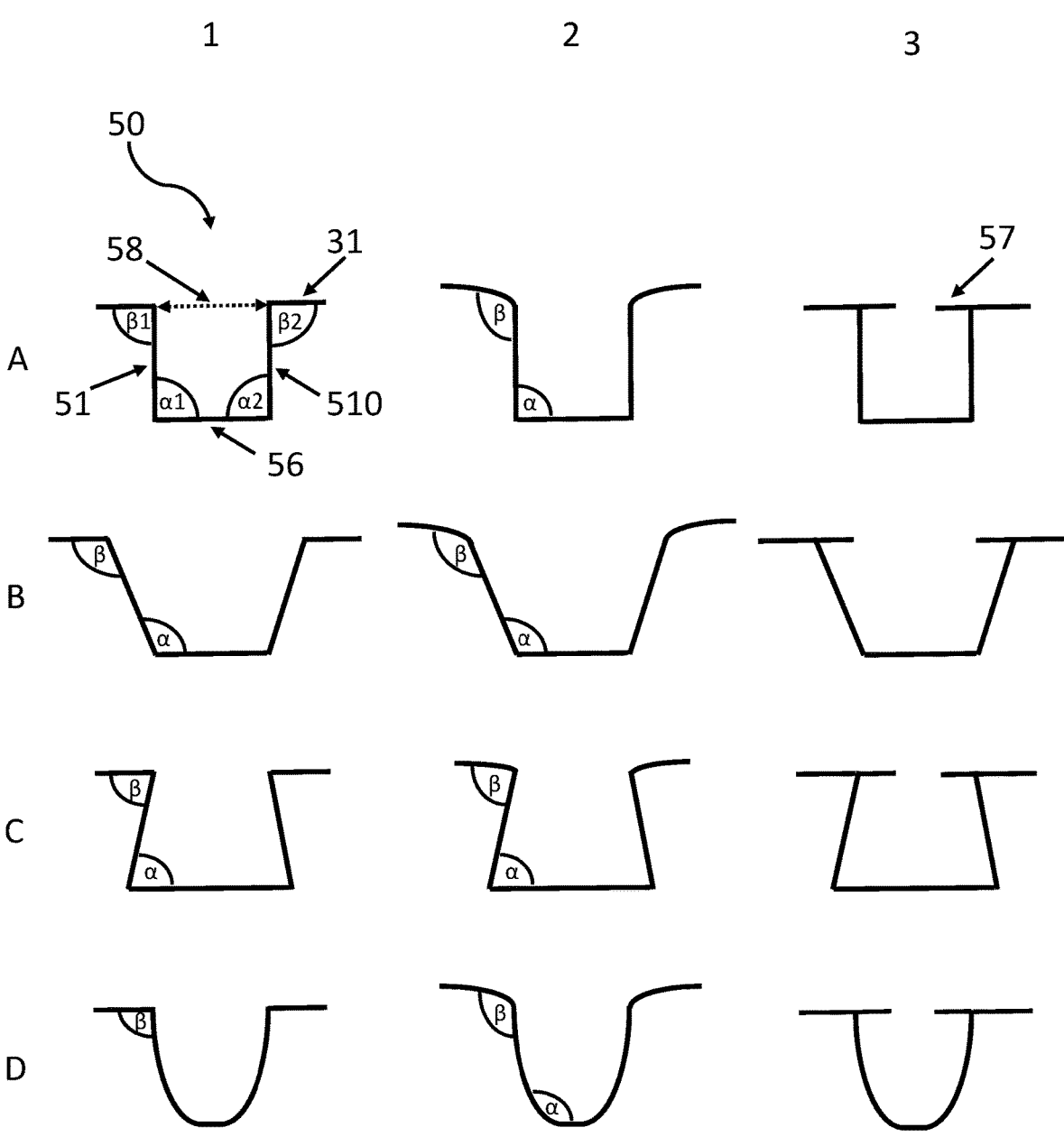

FIGS. 10 and 11 show, by way of example, schematic representations of a guide groove 50 in cross section. The guide groove 50 comprises a groove bottom 56, a rear groove edge 51, a front groove edge 510 and a groove width 58.

The guide groove 50 is delimited by the groove bottom 56. In the present exemplary embodiment, the groove bottom 56 has an almost smooth surface. It is also conceivable that the groove bottom 56 has a structure, for example a ribbing. A structure could improve the guiding property, since the ribbing gives the user tactile feedback as regards the guiding in the guide groove 50. For example, the ribbing can also be another regularly or irregularly formed structure. The structure can be formed in the guide groove 50 in such a way that the user, who guides a connection element 80 along the guide groove 50, receives tactile feedback regarding the approach to the receiving element 70. In this example, the structure in the guide groove 50 would be arranged such that the structure in the regions of the guide groove 50 closer to the receiving element 70 is increasingly or decreasingly more regular or more irregular.

The guide groove 50 is laterally delimited by the rear groove edge 51 and the front groove edge 510. As will be seen from FIG. 10/11, the groove edge 51, 510 can extend for example rectilinearly from the outer side 31 to the groove bottom 56. A convex or concave curvature of the groove edge 51 and/or 510 is also conceivable.

An angle α1 and an angle α2 describe at which angle the rear groove edge 51 and the front groove edge 510 are arranged at the groove bottom 56. The angle α1 and the angle α2 can be constant. The angle α1 and/or the angle α2 can have different values in the profile of the guide groove. The angle α1 and the angle α2 are independent of each other.

The groove edge 51, 510 can be arranged at an angle α1, α2 of 90° to the groove bottom 56 (FIG. 11A).

The groove edge 51, 510 is preferably inclined, preferably outwardly inclined (FIG. 10 and FIG. 11 B). For example, the groove edge 51, 510 can be arranged on the groove bottom 56 at an obtuse angle α1, α2. The angle α1, α2 can be 90° to 180°, preferably 90° to 135°. In advantageous embodiments, the angle α2 can be for example between 90° and 95° and the angle α1 can vary between 90° and 135°.

An angle α1, α2>90° is suitable when the face part 30 is produced by injection molding, since the face part 30 can then be easily released from the mold. Moreover, an outwardly inclined guide groove 50 is easier to clean.

The angle α1, α2 can also be smaller than 90°, such that the groove edge 51, 510 is arranged with an inward inclination (see FIG. 11 C).

An embodiment with an angle α1, α2<90° could be advantageous, since an inwardly inclined groove edge 51, 510 may provide better and more reliable guiding properties for the connection element 80.

An inwardly protruding overhang 57 at the groove edge 51 and/or at the groove edge 510 could also be particularly advantageous for the use for example (see FIG. 11A-D, row 3). An inwardly protruding overhang 57 could improve the guiding property of the guide groove 50, since components of the connection element 80, for example the button plate described below, could be guided along between overhang 57 and groove bottom 56, which can increase the safety of the guiding.

The transition from the groove bottom 56 to the groove edge 51, 510 can be polygonal (FIGS. 11 A-C) or rounded (FIG. 11 D). A rounded transition may be advantageous in terms of cleaning.

An angle β1 and an angle β2 describe at which angle the rear groove edge 51 and the front groove edge 510 are arranged with respect to the outer side 31. The angles β1 and β2 can be constant, for example. It is also conceivable that the angle β1 and/or the angle β2 have different values in the profile of the guide groove. The angle β1 and the angle β2 are independent of each other.

The groove edge 51, 510 can drop at an angle β1, β2 of 90° from the outer side 31 (FIG. 11A).

In the present exemplary embodiment, the angle β1, β2 is greater than 90° (FIGS. 10 and 11 B+D). For example, the groove edge 51, 510 can be arranged at an obtuse angle β1, β2 to the outer side 31. The angle β1, β2 can be 90° to 180°, preferably 90° to 135°. In advantageous embodiments, the angle β2 can for example be between 90 and 100°, and the angle β1 can vary between 90 and 135°.

It is also conceivable that the groove edge 51, 510 is arranged at an acute angle β1, β2 of for example 45 to 90° to the outer side 31 (FIG. 11 C).

The transition from the outer side 31 to the groove edge 51, 510 can be polygonal (see FIG. 11, row 1+3) or rounded (see FIG. 11, row 2). A rounded transition may be advantageous in terms of cleaning.

The groove width 58 of the guide groove 50 is dependent on the orientation of the groove edge 51, 510 and the angles α1, α2 and β1, β2 and also the width of the groove bottom 56. In the present exemplary embodiment, the groove width 58 is wider than the groove bottom 56 (FIGS. 10 and 11 B). The groove width 58 can also be narrower (FIG. 11 C) or the same width (FIG. 11A) as the groove bottom 56. The ratio of the groove width 58 to the width of the groove bottom 56 can be constant, for example. However, the ratio can also change in the profile of the guide groove 50.

Figure 12:
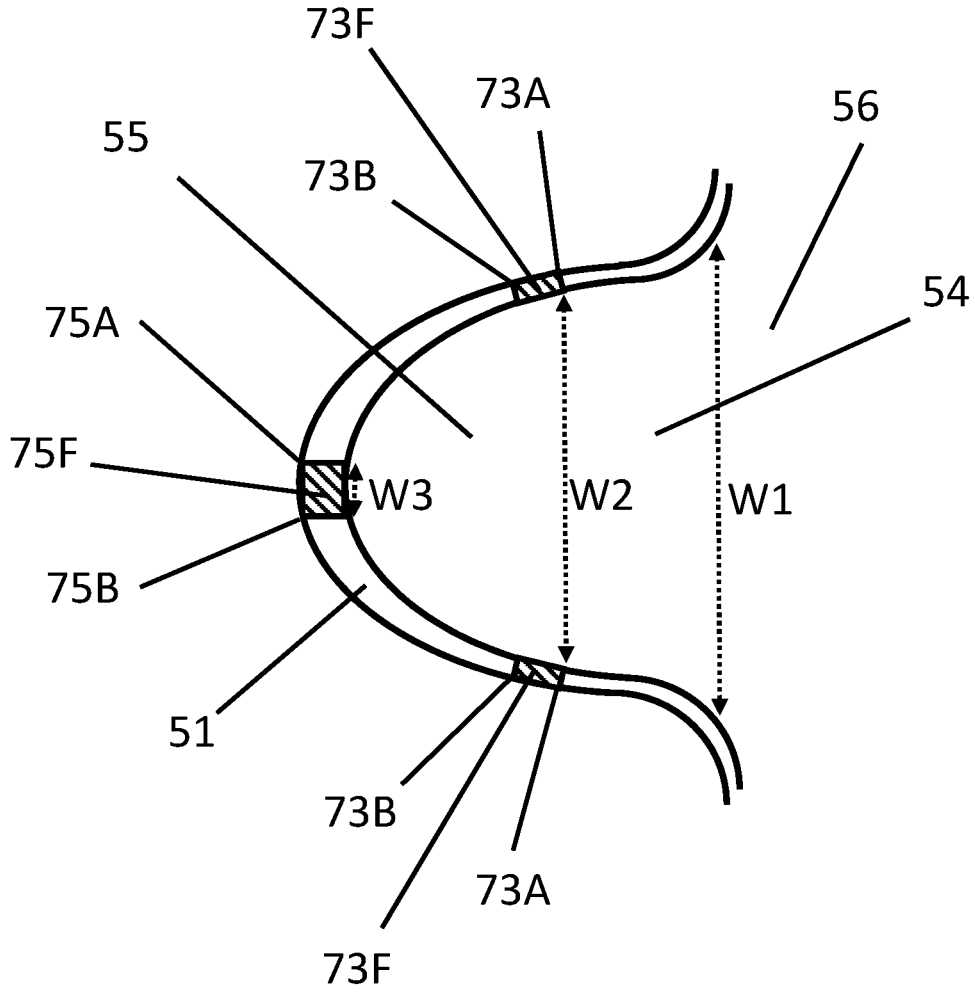
FIG. 12: a schematic overview of a rear groove edge in the region of a groove bay, in a plan view.

FIG. 12 shows, in a plan view, a schematic overview of the rear groove edge 51 in the region of the groove bay 54. The receiving element 70 spanning this region, and described hereinbelow, is not shown.

The groove bottom 56 of the groove bay 54 has different widths. The groove bottom 56 of the groove bay 54 decreases in width in the horizontal. This means that a first groove bay width W1 is greater than a second groove bay width W2, and the groove bay width W2 is greater than a third groove bay width W3.

The groove bay width W1 is the width of the groove bottom 56 that arises from the horizontal profile of the rear groove edge 51 between the groove width 58B and the groove width 58D. By definition, the groove bay width W2 is the width of the groove bottom 56 between two front web extensions 73A (described further below). The groove bay width W3 is by definition the width of the groove bottom 56 between an upper central web extension 75A and a lower central web extension 75B (described further below).

The end region 55 of the guide groove 50, at the horizontal end of the guide groove 50, lies in the groove bay 54 between a groove bay width W2 and a groove bay width W3.

The height of the rear groove edge 51, and thus the depression 59 of the guide groove 50, can be constant in the region of the groove bay 54. Advantageously, and as shown in this exemplary embodiment, the rear groove edge 51 increases in height in the region of the groove bay 54. The height of the rear groove edge 51 can increase successively from the width 1 to the width 3 in the course of the groove bay 54.

As a result of the heightened groove edge 51 in the region of the groove bay 54, and therefore also in the end region 55, the three-dimensional extent of the guide groove 50 increase in this end region 55.

The guide groove 50 and in particular the groove edges 51, 510 allow the user and/or patient to reach the end region 55. The user and/or patient can reach the end region 55 for example by feel.

It is envisioned in particular that the user and/or the patient can move his or her fingers, or in particular the connection element 80 described hereinbelow, along the groove edge 51 and/or 510 and thereby reach the end region 55.

In the present exemplary embodiment, the horizontal profile of the guide groove 50 is bay-shaped. This allows the user and/or the patient to reach an end region 55, which lies in the groove bay 54, by following the rear groove edge 51.

For example, the user and/or the patient can guide a connection element 80 (described hereinbelow) along the rear groove edge 51 to the end region 55, where the connection element 80, in a manner described below, can be fastened by being received in a receiving element 70 on the respiratory mask 100.

In this exemplary embodiment, as will be seen from FIG. 4, two anchor points 60/61 are arranged at the two lower corner points 43/44 of the face part 30. It is also conceivable that further anchor points are arranged on the face part 30. Further anchor points could also be arranged to one side of the lower corner points 43/44, for example lying farther above 310.

The anchor points 60/61 are arranged to both sides of the plane of symmetry 300 and accordingly constitute, as described above, a left anchor point 60 and a right anchor point 61. The anchor points 60/61 are preferably at a maximum distance away from the plane of symmetry 300.

It will be clear from FIG. 5 that the, for example, two anchor points 60/61 are arranged between the central plane 450 and the rear plane 400. The anchor points 60/61 each comprise a receiving element 70 and a connection element 80.

The outer side 31 comprises a respective receiving element 70 at the anchor points 60/61. FIGS. 13 to 16 show an exemplary embodiment of a receiving element 70.

Figure 13:
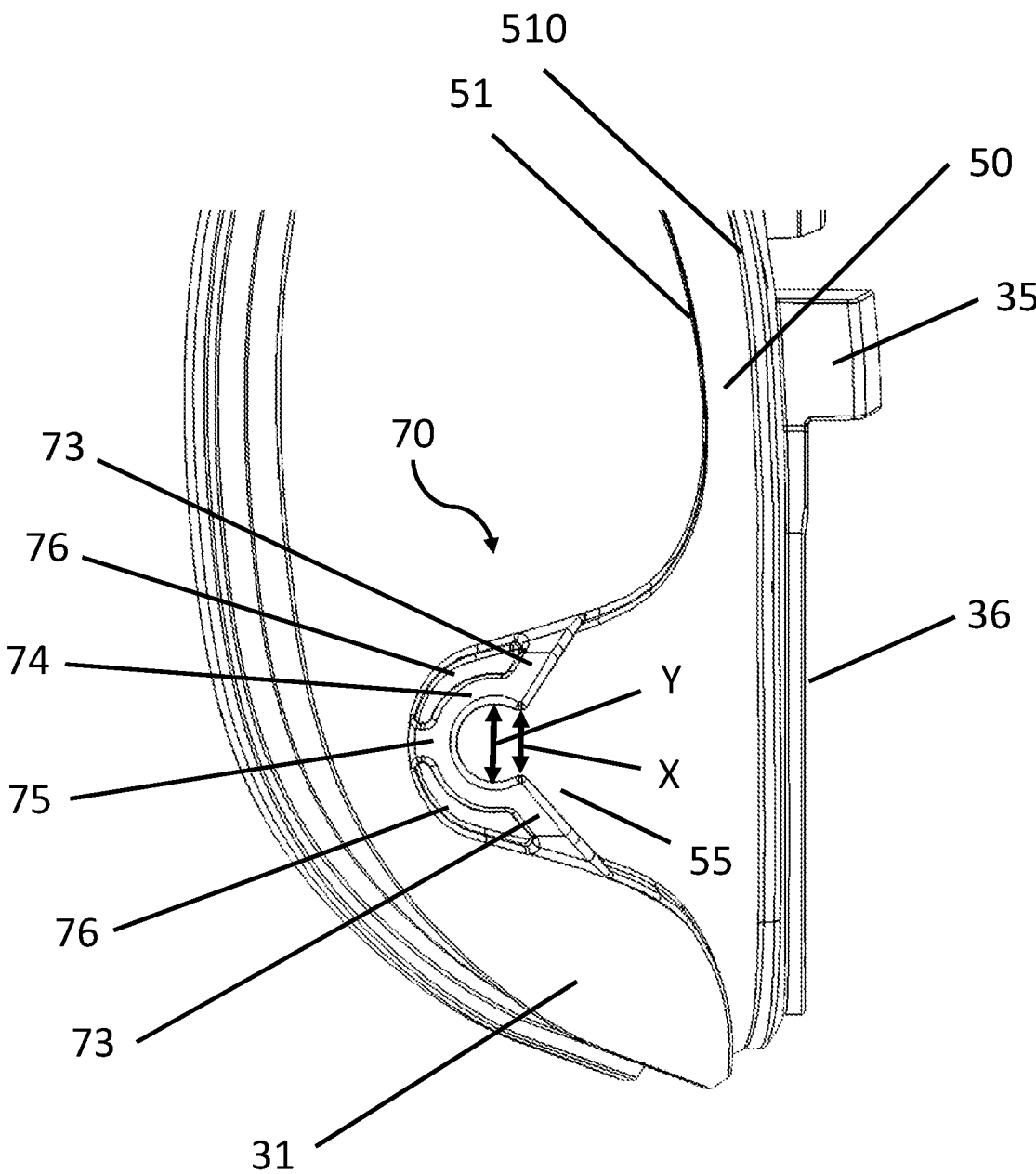
FIG. 13: a detail of a face part in a plan view, in order to illustrate a receiving element.

FIG. 13 shows an overview of the receiving element 70 in a plan view. The receiving element 70 is an integral part of the outer side 31 of the rear groove edge 51.

The receiving element 70 is advantageously produced from a material which, on the one hand, has a certain flexibility and low susceptibility to stress cracks and, on the other hand, has sufficient stability. The receiving element 70 is for example produced in one piece and from the same material as the face part 30. A two-part design is also conceivable. The receiving element 70 is produced from polyamide PA12, for example. Polyamide PA12 is very stable, has a low susceptibility to stress cracks and is resistant to temperature.

The receiving element 70 is arranged between the width W2 and the width W3 of the groove bay 54 (see FIG. 12) and spans the end region 55 of the guide groove 50.

In the present exemplary embodiment, the receiving element 70 comprises two webs 73, a bridge 74, a receiving diameter Y and a receiving opening X. The receiving element can moreover comprise, for example, at least one central web 75 and at least one aperture 76, preferably two apertures 76.

Figure 14:
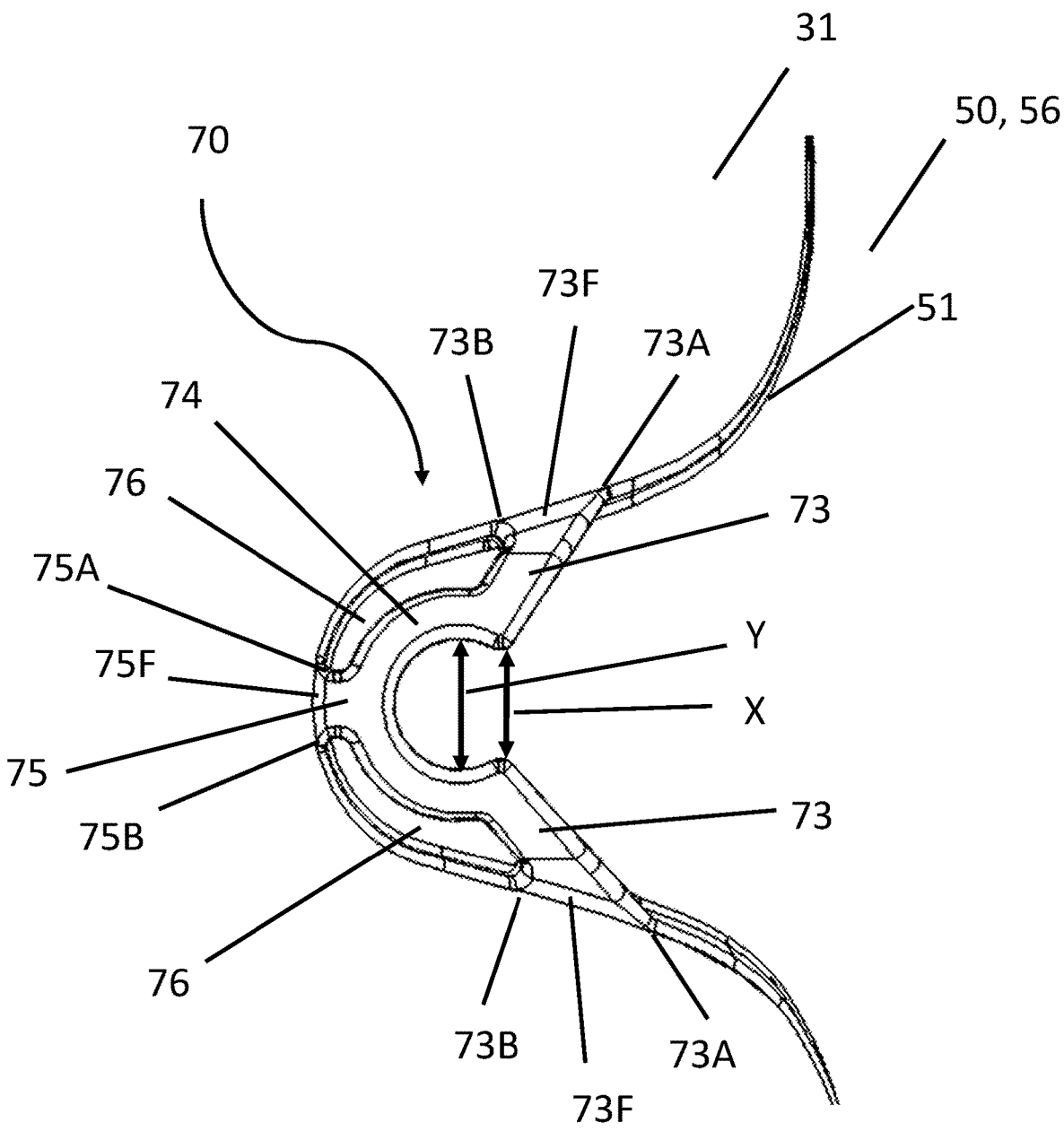
FIG. 14: a receiving element in detail in a plan view.
Figure 15:
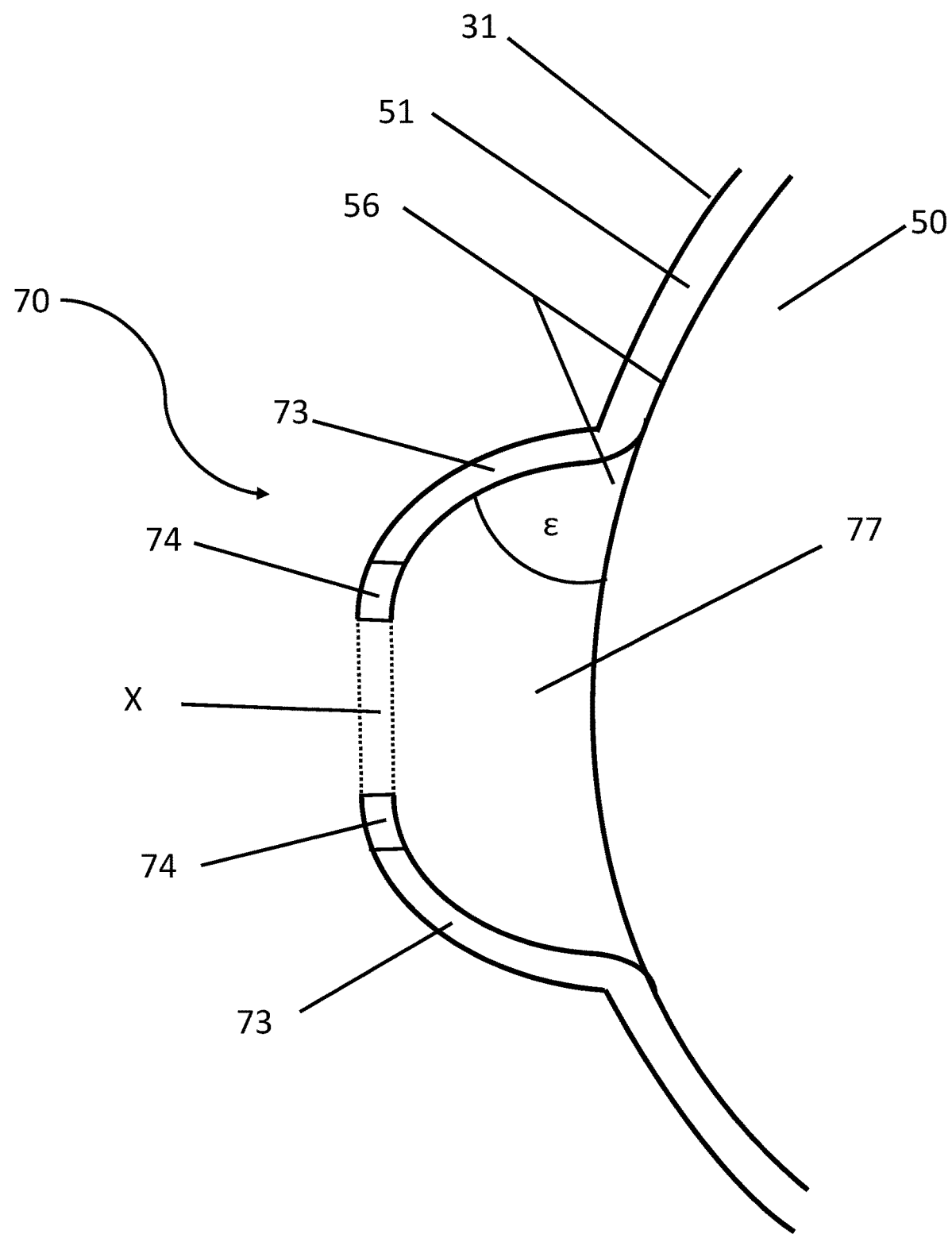
FIG. 15: a schematic depiction of a receiving element from the front.
Figure 16:
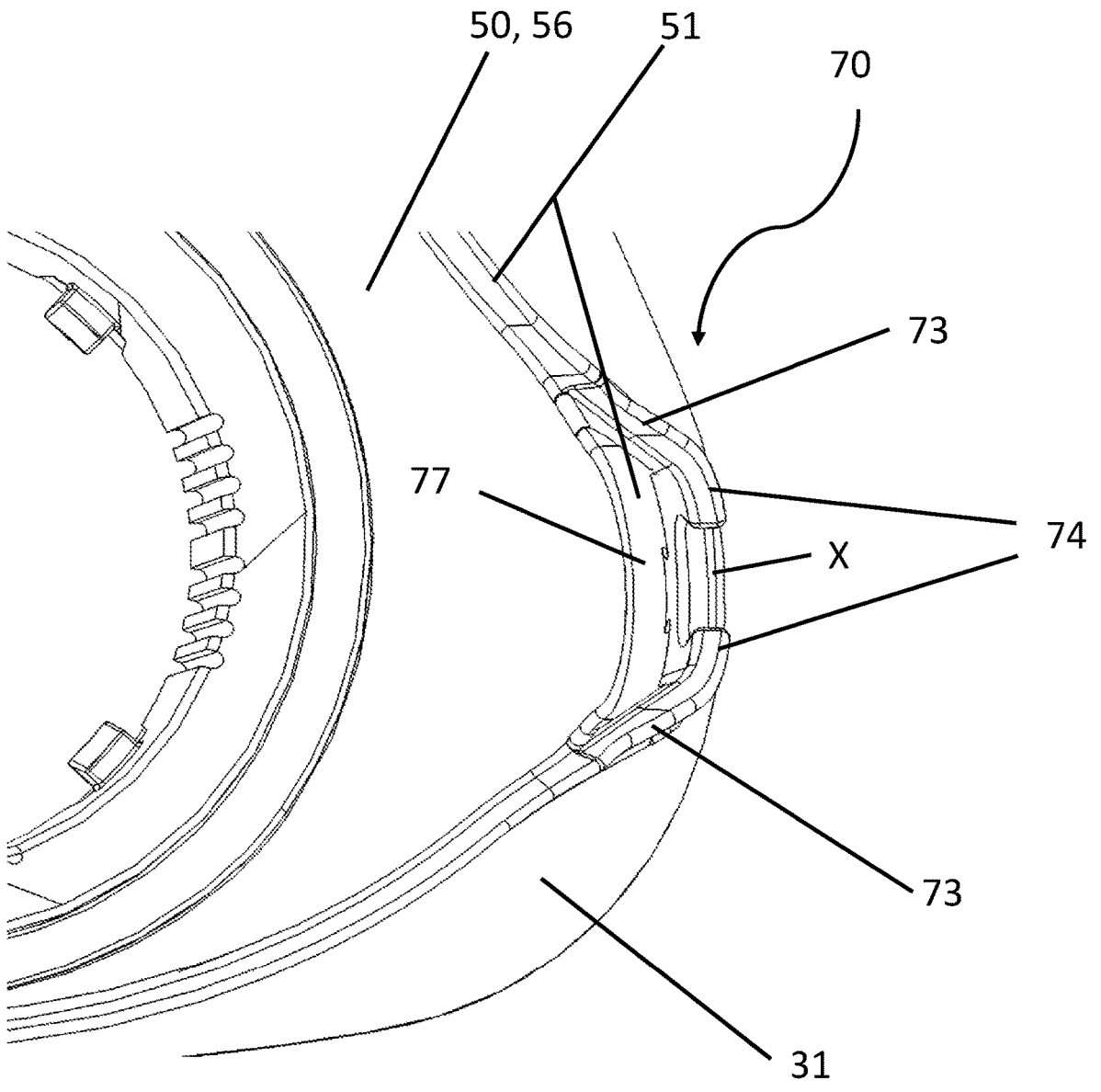
FIG. 16: a detail of a face part from the front, in order to illustrate a receiving element 70 from the front 520.

FIG. 14 shows a detailed plan view of the receiving element 70. FIG. 15 shows a schematic view of the receiving element 70 from the front 520. FIG. 16 shows a detail of a face part 30 from the front 520, in order to illustrate a receiving element 70 from the front 520.

The webs 73 protrude from the rear groove edge 51. The webs 73 rise over the groove bottom 56 of the guide groove 50 and have substantially no contact with the groove bottom 56 (see FIG. 15). The webs are connected to the rear groove edge 51 via web extension surfaces 73F.

The web extension surfaces 73F are between 3 mm and 6 mm wide, for example 5 mm wide, and extend from a front web extension 73A to a rear web extension 73B.

The width of the webs 73 can be wider at the web extension surface 73F (for example 5 mm). The width of the webs 73 can decrease in width, in their further course, to a range from 4 mm to 1 mm. The webs have a width of substantially 3.3 mm, for example.

The webs 73 can have a constant material thickness, for example. The webs 73 are between 1 mm and 4 mm thick, for example 2 mm thick. The webs 73 can be 2 mm to 20 mm long, for example 14 mm long. The webs 73 are matched to one another in width, length and thickness in such a way that sufficient flexibility is obtained.

The webs 73 can have a curved or arching profile, for example. This means that the webs do not have to run in a straight line.

An angle ε describes at which angle the webs 73 are arranged to the groove bottom 56 (see FIG. 15). The webs 73 can be arranged at an angle of ε of 90° to the groove bottom 56. Preferably, the webs 73 are arranged at an angle ε of 30° to 90°, for example at an angle ε of 30° to 60°, to the groove bottom 56.

A bridge 74 is arranged adjacent to the webs 73. Bridge 74 and webs 73 are for example designed in one piece.

In this exemplary embodiment, the bridge 74 is equivalent in width and thickness to the webs 73, whereas the bridge 74 can be longer than the webs 73.

The bridge 74 is 1 mm to 4 mm thick, for example 2 mm thick. The bridge 74 can be 10 mm to 30 mm long, for example 14 mm long. The bridge 74 is 1 mm to 4 mm wide, for example 2.3 mm wide.

The bridge 74 is circular, for example. The bridge 74 is not designed as a closed circle and is instead interrupted by a receiving opening X. The receiving opening X is between 3 mm and 12 mm wide, preferably between 5 mm and 8 mm wide, for example 5.8 mm wide.

The receiving opening X is oriented to the front 520. As a result of the receiving opening X, the bridge 74 has an approximately semicircular shape. The receiving opening X is designed to receive a neck 93 (described hereinbelow) of the connection element 80.

The receiving opening X is slightly smaller than the diameter of the neck 93D, such that the neck can be received simply by application of pressure and by slight resilience of the receiving element 70.

The bridge 74 has a receiving diameter Y. The receiving diameter Y of the bridge 74 is between 3 mm and 12 mm, preferably between 5 mm and 8 mm, for example 6.2 mm. The receiving diameter Y is slightly greater than the receiving opening X. The receiving diameter Y is configured to receive a neck 91 (described hereinbelow) of the connection element 80. The receiving diameter Y is slightly greater than the diameter of the neck 93D.

By virtue of the fact that the webs 73 are arc-shaped and rise above the groove bottom 56 with the angle ε, the receiving space 77 between webs 73, bridge 74 and groove bottom 56 is obtained (see FIG. 15 and FIG. 16).

The receiving space 77 is located at the end region 55 (see FIG. 13). The receiving space 77 has a height of 2 mm to 8 mm, for example 4 mm. The receiving space 77 is configured to receive a button plate 91 (described hereinbelow) including the overhang 92 of the connection element 80. The depth of the receiving space 77 is accordingly greater than the length of the button plate 91L.

The at least one central web 75 connects the bridge 74 to the outer side 31. In the present exemplary embodiment, the central web 75 is located at the halfway point of the semicircular bridge 74 (FIG. 13).

It will be clear from FIG. 14 that the central web 75 is connected to the rear groove edge 51 via a central web extension surface 75F. The central web extension surface 75F is between 1 and 6 mm wide, for example 3 mm wide, and extends from an upper central web extension 75A to a lower central web extension 75B. The width of the central web 75 can be wider at the central web extension surface 75F, for example 3 mm, and in its further course can decrease in width to 2 mm, for example.

The width of the central web extension surface 75F from the upper central web extension 75A to a lower central web extension 75B corresponds to the above-described width W3 of the groove funnel (see FIG. 12).

The at least one aperture 76 or, in this exemplary embodiment, the two apertures 76 are arranged between the central web 75 and the webs 73. The apertures 76 permit easier construction and save on material. Moreover, depending on the material chosen, a flexibility can be obtained which ensures that the connection element 80 is easy to latch in place and release.

It is also conceivable that the receiving element 70 is designed without apertures 76 and central web 75. In this case, the rear groove edge 51 and the outer side 31 would transition directly into the bridge 74 and webs 73 (not shown).

Figure 17:
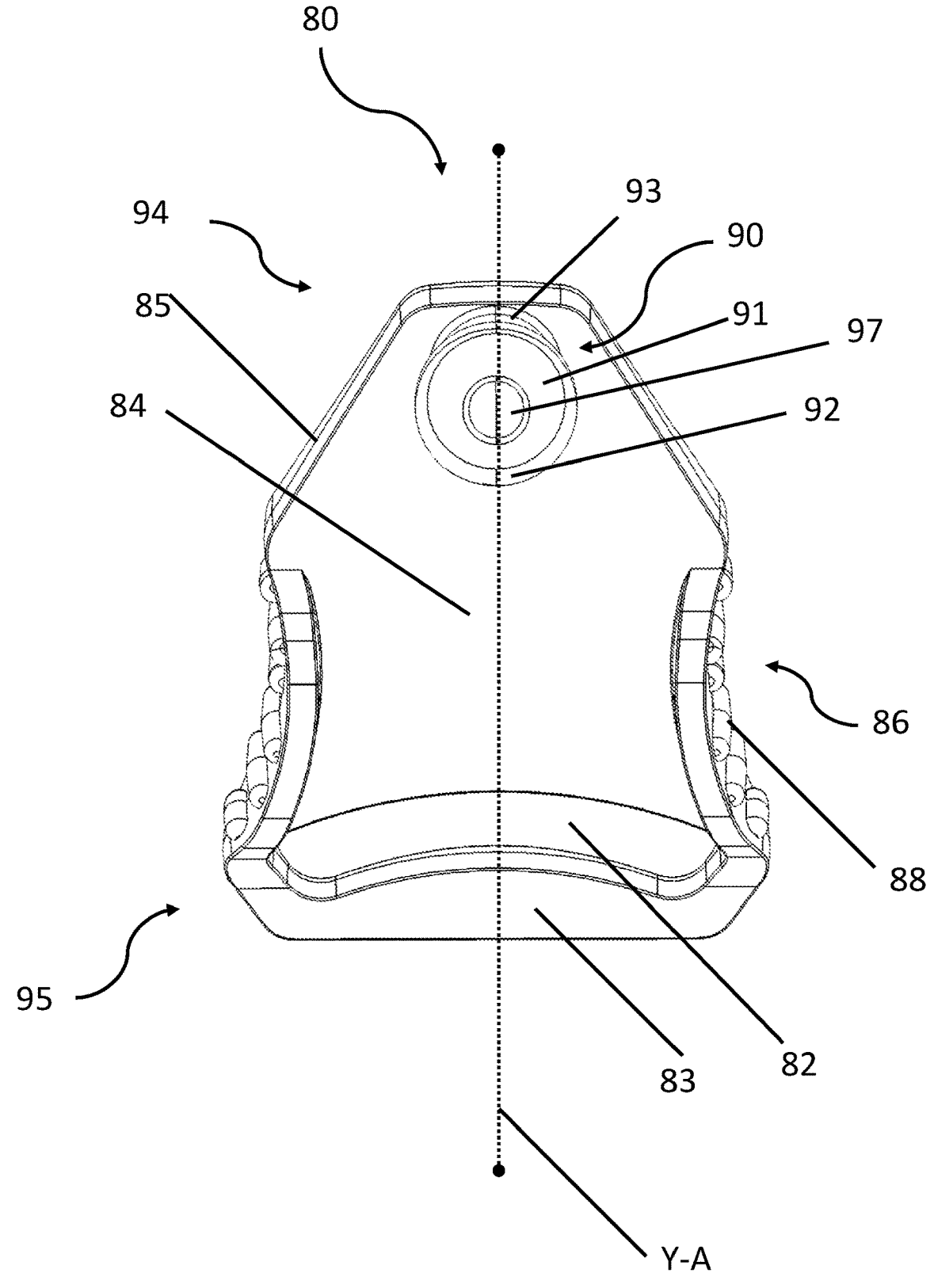
FIG. 17: a connection element in a plan view from the rear.
Figure 18:
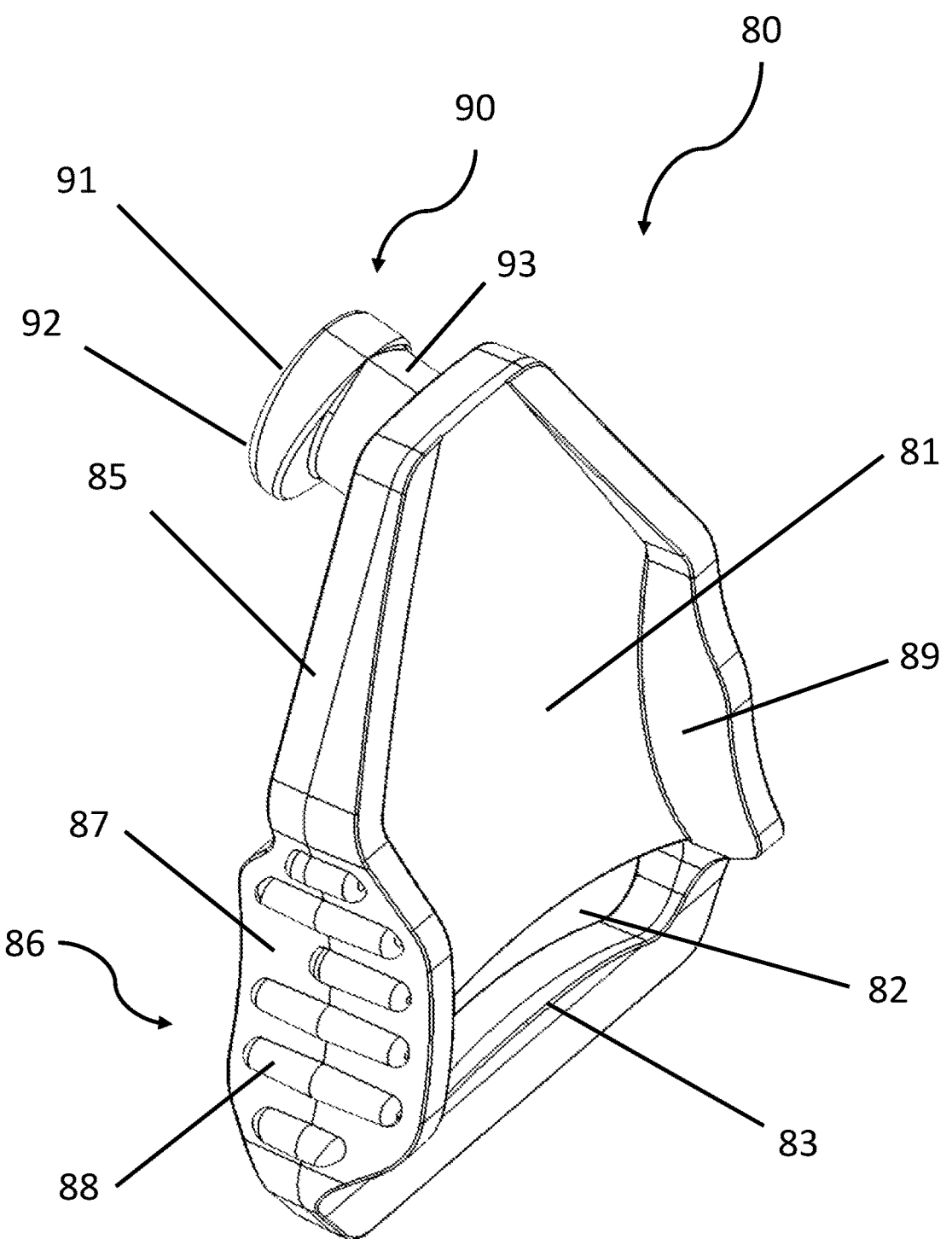
FIG. 18: a connection element in a perspective view obliquely from the front.
Figure 19:
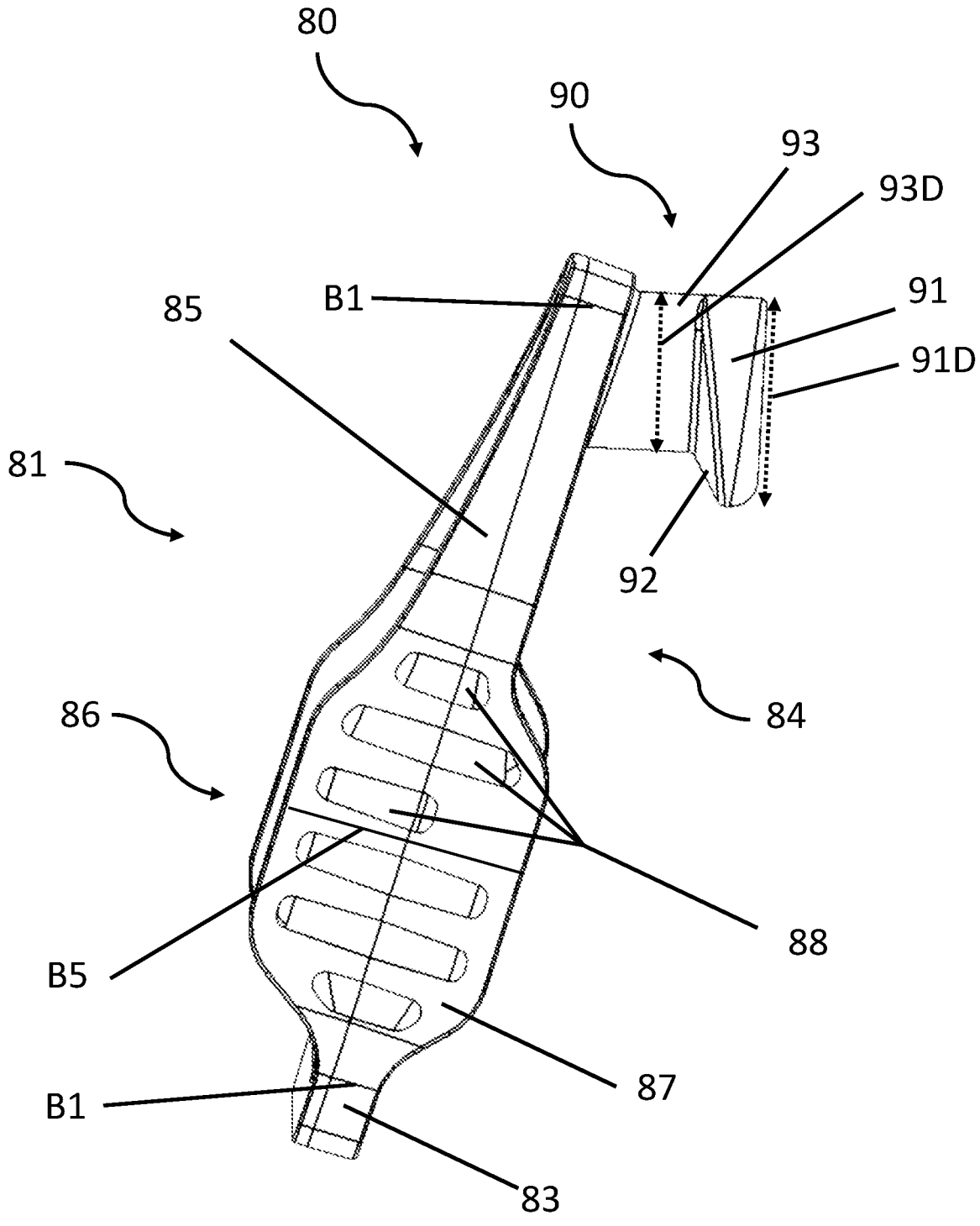
FIG. 19: a connection element from the side.

FIGS. 17 to 19 show an exemplary embodiment of a connection element 80 according to the invention. FIG. 17 shows a connection element 80 in a plan view from behind 420. FIG. 18 shows a connection element 80 in a perspective view obliquely from the front 520. FIG. 19 shows a connection element 80 from the side.

The connection element 80 is a releasable component of the respiratory mask 100. The connection element 80 can be produced from any desired material that has sufficient stability.

The connection element 80 is preferably produced from the same material as the face part 30. The connection element 80 is preferably produced from a rigid plastic. Suitable plastics comprise, for example, polyamides, polycarbonates, polyoxymethylenes, polysulfones and polypropylenes. For example, the connection element 80 is produced from polyamide PA12. The connection element 80 is for example produced entirely from polyamide PA12. However, it is also conceivable that different component parts of the connection element 80 are made of different materials.

FIG. 17 shows, by way of example, an embodiment of the connection element 80 in a plan view from behind 420. This view shows the surface that is directed toward the face part 30 (not shown) after the connection element 80 is fastened to the receiving element 70. By definition, this surface is the inner base surface 84 of the connection element 80. In this embodiment, the ace 80 has a hexagonal base surface. The base surface can also have any other suitable shape.

The base surface is flat. Thus, in this embodiment, the base surface of the connection element 80 is not curved or arc-shaped. However, it is also conceivable that the base surface of the connection element 80 has a curved or arc-shaped design.

The connection element 80 comprises a fastening element 90. By definition, the fastening element 90 is located at the upper end 94 of the connection element 80. The connection element 80 moreover comprises a holding web 83 and a cutout 82. By definition, holding web 83 and cutout 82 are located at the lower end 95 of the connection element 80. Thus, fastening element 90 and holding web 83 lie on mutually opposite sides of the connection element.

The connection element 80 can be manually fastened to the face part 30, more specifically on the receiving element 70 of the face part 30, via the fastening element 90. The fastening is reversible; that is to say the fastening can be manually produced at any time and released again, without the material undergoing a permanent change.

A harness 96 (not shown) can extend through the cutout 82. The harness 96 can extend over the holding web 83 are serves to fasten the respiratory mask 100 to the head (not shown) of a user and/or patient.

In this embodiment, the connection element 80 is configured axially symmetrically about a y axis.

The connection element 80 has a length in a range from 100 mm to 10 mm, preferably from 50 mm to 20 mm, for example 35 mm. The connection element 80 has a maximum width of from 80 mm to 10 mm, preferably from 40 to 20 mm, for example 27 cm. The base surface of the ace 80 has a thickness of from 1 mm to 3 mm, for example 2 mm.

FIG. 18 shows a connection element 80 in a perspective view obliquely from the front 520. It will be seen from FIG. 18 that the connection element 80 comprises a circumferential side wall 85 with at least one but preferably two grip recesses 86. The grip recesses 86 comprise at least one structural element 88.

The connection element 80 has a total length of 35 mm for example (see above). The grip recesses 86 have a length of 5 mm to 30 mm, preferably of 10 to 20 mm, for example 17 mm. In other words, the grip recess 86 extends preferably over 50% of the length of the connection element 80.

FIG. 19 shows a connection element 80 from the side. It will be seen from FIG. 19 that the side wall 85 can be designed with a varying width. The width of the side wall 85 lies in a range from 20 mm to 1 mm, preferably 15 mm to 1 mm. In this exemplary embodiment, the side wall 85 at the upper end 94 is ca. 2 mm wide (B1) and increases in width.

The side wall 85 has the greatest width of ca. 10 mm (B5) at the height of the grip recesses 86. After the grip recesses 86, the side wall 85 narrows again to its initial width (b1). Thus, in this exemplary embodiment, the grip recess 86 is about 5 times as wide as the side wall 85 at the upper end 85 or at the lower end 96 of the connection element 80.

The grip recesses 86 allow the connection element 80 to be gripped with two fingers, for example index finger and thumb. The length and width of the grip recess 86 is preferably chosen such that the user and/or the patient can grip the connection element 80 firmly and safely with two fingers.

The grip recess outer wall 87, i.e., the side wall 85 at the height of the grip recesses 86, has at least one structural element 88, preferably several of them, for example six structural elements 88. The structural elements 88 serve to increase the grippability of the grip recesses 86.

The at least one structural element 88 comprises, for example, at least one elevation, e.g. in the form of ribs, corrugations, lattice structures, meshes, dots or the like. In the present embodiment, the structural elements are in the form of rib-like elevations, which are arranged on the grip recess outer wall 87.

The grippability of the grip recesses 86 is increased via the structural elements 88 of the grip recess outer wall 87. The shape of the structural elements 88 is chosen such that they are optimal in terms of grippability, comfort and stability.

By contrast, the grip recess inner wall 89 is preferably smooth (see FIG. 18). A smooth design of the grip recess inner wall 89 is advantageous since it saves on material and entails less weight, and the grip recess inner wall 89 can be cleaned more easily and more efficiently.

Figure 20:
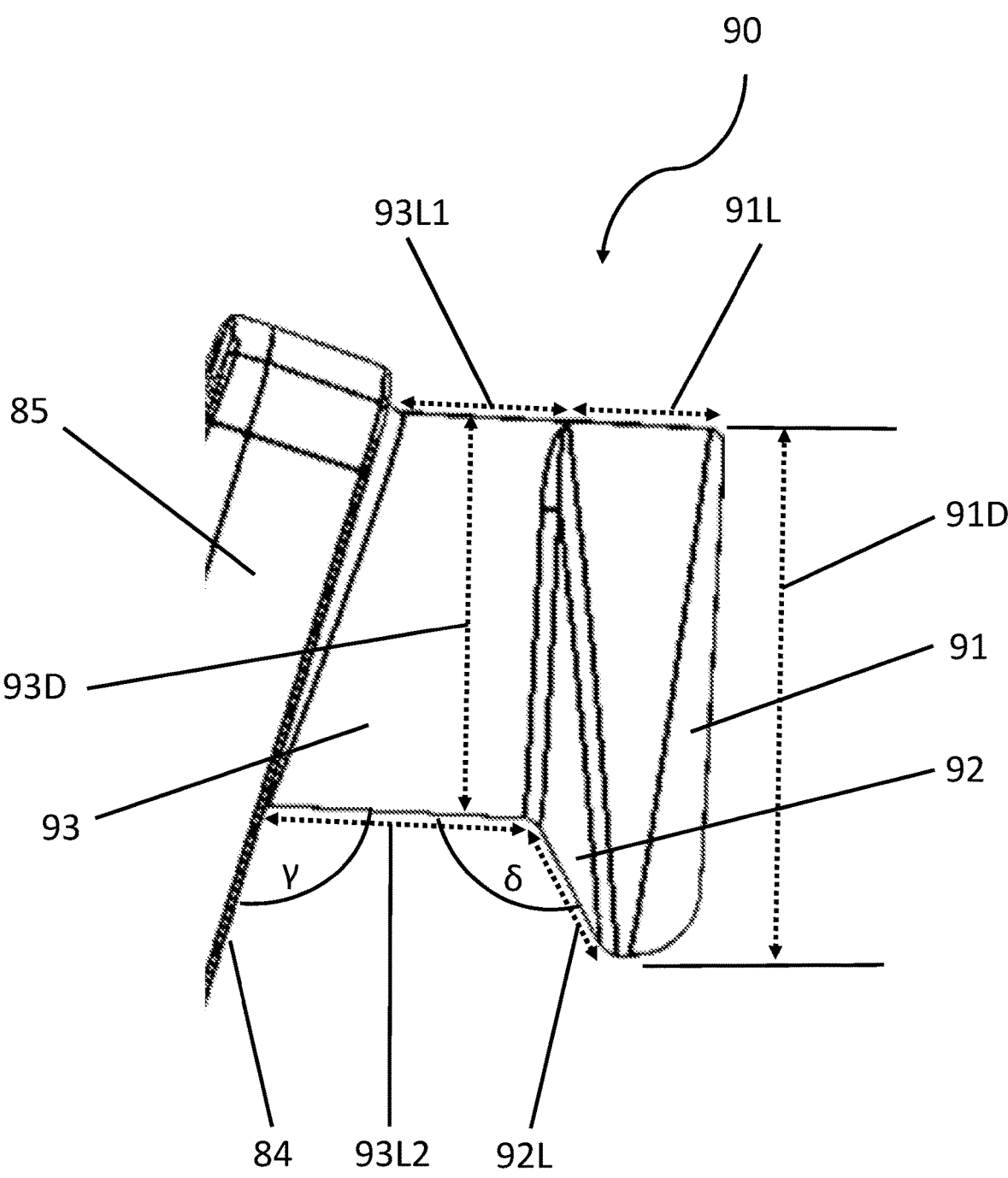
FIG. 20: the fastening element in detail.

The connection element 80 comprises a fastening element 90. FIG. 20 shows the fastening element 90 in detail. Connection element 80 and fastening element 90 can be in one piece or in two pieces. In this exemplary embodiment, connection element 80 and fastening element 90 are formed in one piece. The fastening element 90 is a constituent part of the connection element 80, and connection element 80 and fastening element 90 are made of the same material.

The fastening element 90 comprises a button plate 91, an overhang 92 and a neck 93. The button plate 91 is connected to the inner base surface 84 of the connection element 80 via the neck 93.

The neck 93 is round or rounded and has a maximum diameter 93D of 3 mm to 12 mm, for example 6 mm. The diameter 93D is such that the neck 93 can be guided only with slight pressure through the receiving opening X (FIG. 13). The diameter 93D is such that it is slightly greater than the receiving opening X. The diameter 93D is such that it is slightly smaller than the receiving diameter Y (FIG. 13).

The button plate 91 is round or rounded and has a maximum diameter 91D of 3 mm to 14 mm, for example 8 mm. The diameter of the button plate 91D is greater than the diameter of the neck 93D.

As the neck 93 is guided through the receiving opening X into the receiving diameter Y, the button plate 91 enters the receiving space 77. The button plate 91 serves for fixing in the receiving space 77 of the receiving element 70 (FIG. 15). A hollow 97, open at one side, can advantageously be arranged in the button plate 91. The hollow 97 makes it possible to avoid accumulation of material in the plastic component of the button plate.

It will be clear from FIG. 20 that the diameter of the button plate 91 is greater than the diameter of the neck 93D, and that the transition from neck 93 to button plate 91 is straight at the upper side. Since the diameter of the button plate 91D is greater than the diameter of the neck 93D, the button plate 91 protrudes beyond the diameter of the neck 93D, and an overhang 92 is formed. The button plate 91 thus comprises the overhang 92, which protrudes beyond the circumference of the neck 93D.

The diameter of the neck 93D gradually transitions, along a maximum length 92L of the overhang, into the diameter of the button plate 91D. An angle δ describes at which angle the overhang 92 is arranged to the neck 93. The angle δ can be 90 to 135°, for example.

The neck 93 has an upper length 93L1 and a lower length 93L2, wherein the upper length 93L1 is smaller than the lower length 93L2. In the view according to FIG. 20, the neck is therefore arranged at an angle γ to the side wall 85. The angle γ can be 90° to 135°, for example.

At the side opposite the fastening element 90, the connection element 80 has a cutout 82 and a holding web 83 (see FIG. 17 and FIG. 18). Thus, cutout 82 and holding web 83 lie at the lower end 95 of the ace 80. The holding web 83 is created by virtue of the base surface of the connection element 80 having the cutout 82. The holding web is designed as part of the side wall 85 of the connection element 80 and is arranged at the lower end 95 of the connection element 80.

The cutout 82 is configured in such a way that it is able to receive a harness 96 (not shown). The harness 96 can extend with its flat side through the cutout and over the holding web 83. In terms of size and shape, the cutout 82 is configured such that the harness 96 can be guided easily and safely through the cutout. In this embodiment, the cutout 82 is designed as an elongate opening. The cutout has a crescent-shaped curve.

The cutout 82 is between 80 mm and 10 mm wide, preferably between 40 mm ad 15 mm wide, for example 22 mm wide. The cutout 82 is between 25 mm and 2 mm high, preferably between 10 mm and 3 mm high, for example 4.1 mm high. Advantageously, the cutout 82 is sufficiently wide to be able to receive a suitable harness 96. Furthermore, the height of the cutout 82 is such that the harness 96 can be guided comfortably through the cutout.

The cutout 82 is delimited by the base surface of the connection element 80. At the lower end 95 of the connection element 80, the cutout 82 is delimited by the side wall 85. The side wall 85 at the lower end 95 comprises the holding web 83. To put it another way, the holding web 83 is formed because the base surface of the connection element 80 has a cutout 82.

In terms of size and shape, the holding web 83 is configured in such a way that the harness 96 can be held securely. In this embodiment, the holding web 83 is produced from the same material as the connection element 80. In other words, the holding web 83 is a constituent part of the connection element 80.

The holding web 83 has a varying thickness. The thickness of the holding web lies between 10 mm and 1 mm, for example between 5 mm and 2 mm. The thickness of the holding web is at its greatest, for example 4 mm, at the center and decreases on each side to a width of in each case 2.3 mm. Advantageously, the holding web 83 is of such a width that it withstands the tensile force that a suitable harness 96 can exert on the connection element 80.

Figure 21:
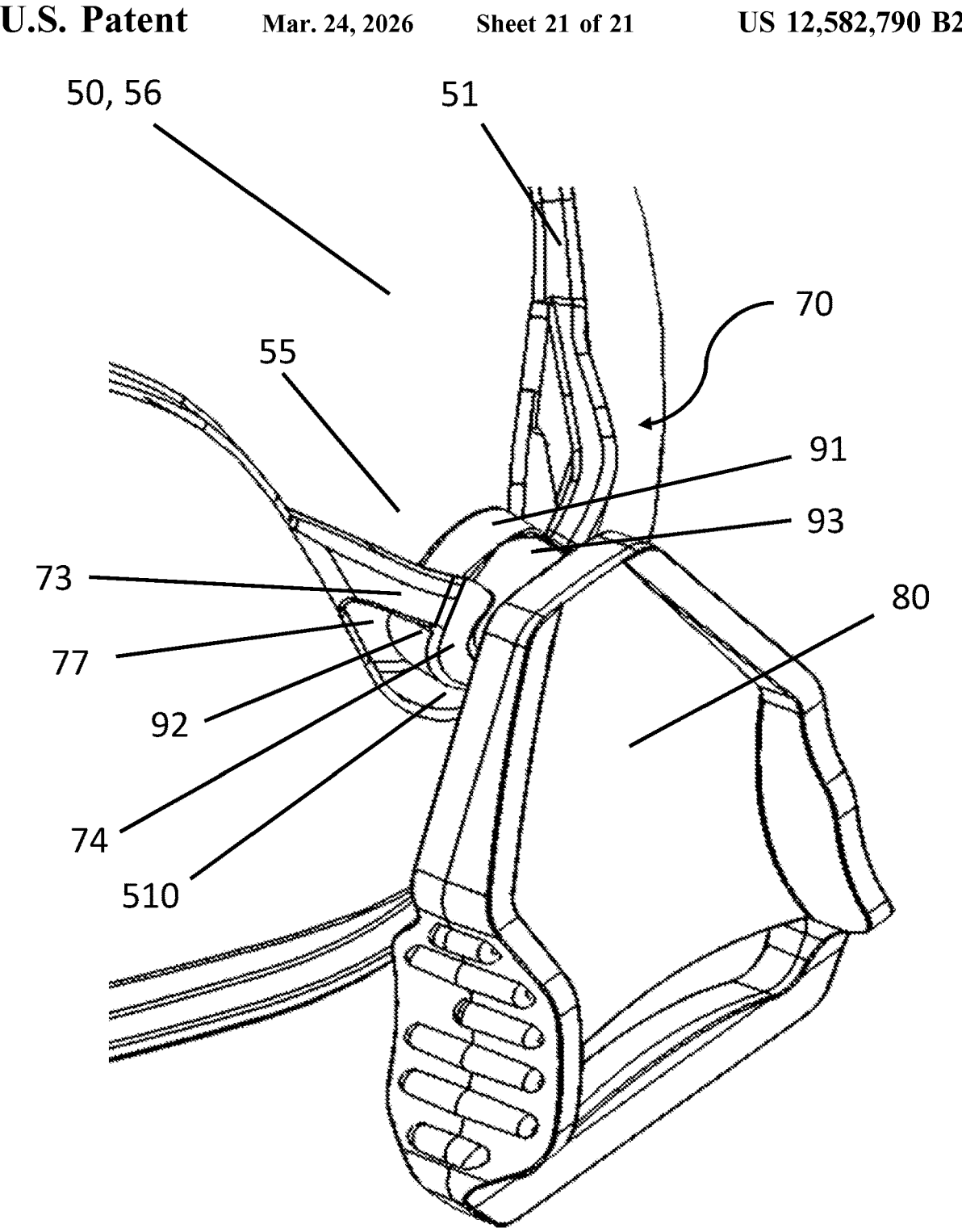
FIG. 21: a connection element, which is connected to the receiving element via the fastening element.

FIG. 21 shows a connection element 80 which is connected to the receiving element 70 via the fastening element 90. The receiving element 70 can be manually connected to the connection element 80. The connection of receiving element 70 and connection element 80 is reversible. After connection of receiving element 70 and connection element 80, the connection element 80 is mounted movably. The connection element 80 is in particular mounted in a rotationally movable manner.

The guide groove 50 allows the user and/or the patient to guide the connection element 80 to the receiving element 70. The fastening element 90 of the connection element 80 can be inserted into the guide groove 50 for example at a groove inlet 52 (FIG. 8). The button plate 91 of the fastening element 90 can then be guided along the groove bottom 56 and the groove edges 51 and/or 510 (FIG. 8). The groove edges 51, 510 serve for orientation purposes and provide guiding in the direction of the end region 55 of the guide groove spanned by the receiving element 70.

When the end region 55 is reached, the button plate 91 of the connection element 80 can enter the receiving space 77, in such a way that the neck 93 reaches through the receiving opening X (FIG. 13/14) into the receiving diameter Y (FIG. 13/14) and is there largely enclosed by the central web 74. In this way, the button plate 91 and the overhang 92 are located in the receiving space 77, which leads to fixing on the receiving element 70.

Since the receiving opening X is minimally smaller than the diameter of the neck 93D, and since the material of the receiving element 80 is slightly flexible, the fastening element 90 can be guided with only slight pressure through the receiving opening X and into the receiving space 77 and the receiving diameter Y. The latching of the fastening element 90 into the receiving element can be felt and heard.

As soon as the fastening element 90 is located in the receiving space 77 and the receiving diameter Y, the fastening element 90 can no longer be removed from these without force.

Since the receiving diameter Y is minimally greater than the diameter of the neck 93D of the fastening element 90, the connection is movable, in particularly rotationally movable.

By connecting the at least two connection elements 90 to the face part 30, the user and/or the patient is able to easily, safely and reversibly fasten the respiratory mask 100 to the head via a harness 96 (not shown) which is located on the connection element 90.

The guide groove 50 affords simple and safe handling by the patient and/or the user. The fastening of the respiratory mask 100 to the head can be successfully accomplished even when the patient and/or the user has impaired vision or sight loss, since there is sufficient tactile feedback concerning the abovementioned properties of the guide groove 50. The orientation of the respiratory mask 100 and the arrangement of the receiving element 80 can be easily detected by touch.

Moreover, the connection of the connection element 80 to the receiving element 90 is easy to handle and does not require particular dexterity. The user can easily and securely grip the connection element 80 at the grip recesses 86, guide it along the guide groove to the receiving element 80 and there press the fastening element 90 with slight pressure through the receiving opening X. The user does not have to operate any further elements in order to do this.

LIST OF REFERENCE SIGNS respiratory mask 100
hose attachment system 150
horizontal plane 200
left 210
right 220
plane of symmetry 300
above 310
below 320
rear plane 400
behind 420
central plane 450
front plane 500
front 520
forehead part 10
forehead cushion 12
upper anchor point 13
connection site 14
transition part 20
face part 30
outer side 31
seal 32
outer edge 33
coupling site 34
intermediate member 35
outlet 36
outlet edge 37
latching element 38
notch element 39
tip 40
inner side 41
bottom left corner point 43
bottom right corner point 44
base 45
guide groove 50
rear groove edge 51
front groove edge 510
groove inlet 52
groove channel 53
groove bay 54
end region 55
groove bottom 56
overhang 57
groove width 58
groove width A 58A
groove width B 58B
groove width C 58C
groove width D 58D
groove width E 58E
groove bay width 1 W1
groove bay width 2 W2
groove bay width 3 W3
angle α α1
angle α α2
angle β β1
angle β β2
depression 59 left anchor point 60
right anchor point 61
receiving element 70
receiving opening X
receiving diameter Y
web 73
web extension surface 73F
front web extension 73A
rear web extension 73B
angle ε ε
bridge 74
central web 75
central web extension surface 75F
upper central web extension 75A
lower central web extension 75B
aperture 76
receiving space 77
connection element 80
outer base surface 81
cutout 82
holding web 83
inner base surface 84
side wall 85
side wall width B1 B1
side wall width B5 B5
grip recess 86
grip recess outer wall 87
structural element 88
grip recess inner wall 89
fastening element 90
button plate 91
diameter of the button plate 91D
length of the button plate 91L
overhang 92
maximum length of the overhang 92L
neck 93
diameter of the neck 93D
upper end 94
lower end 95
harness 96
hollow 97
Y axis Y-A

What is claimed is:

1. A respiratory mask, wherein the respiratory mask comprises a face part having at least one plane of symmetry, a circumferential seal and an outlet, the face part comprising an outer side with at least two anchor points, which are arranged on both sides of the at least one plane of symmetry and each comprise a receiving element for releasable connection to a connection element, which is configured to receive a harness, at least one guide region configured as a guide groove and formed by a depression in the outer side of the face part being arranged adjacent to the receiving element, the guide groove comprising a groove inlet which, through a successive depression, forms a transition from the outer side to a final depression, the groove inlet being arranged at an upper end of the face part.

2. The respiratory mask of claim 1, wherein the guide region is arranged on both sides of the at least one plane of symmetry on the face part.

3. The respiratory mask of claim 1, wherein the guide groove extends over 5% to 100% of a length of the face part.

4. The respiratory mask of claim 1, wherein the guide groove comprises a groove bottom, a rear groove edge, a front groove edge and an end region, the end region being a region of the groove bottom that is enclosed by at least one groove edge.

5. The respiratory mask of claim 4, wherein a surface of the groove bottom and/or a surface of groove edges is smooth and/or structured.

6. The respiratory mask of claim 4, wherein the groove edges are of constant and/or varying height, such that a depression of the guide groove is of constant and/or varying depth, the depression having a depth ranging from 0.5 mm to 6 mm.

7. The respiratory mask of claim 6, wherein the depression is of varying depth, the depression being from 1 mm to 6 mm deep in the end region and being substantially from 0.8 mm to 2 mm deep in other regions of the guide groove.

8. The respiratory mask of claim 1, wherein the guide groove has different groove widths, a first portion being configured as a groove channel with a constant groove width A, which, after the groove channel, successively increases through a groove width B to a groove width C, and wherein, after the groove width C is reached, the groove width successively decreases through a groove width D to a groove width E.

9. The respiratory mask of claim 8, wherein, in a region of the groove width C, a rear groove edge is at a maximum distance from the at least one plane of symmetry, and a front groove edge is arranged at a maximum proximity to the at least one plane of symmetry.

10. The respiratory mask of claim 9, wherein the rear groove edge, in a region between the groove widths B and D, retreats in an arc shape, in such a way that the guide groove in this region is designed as a groove bay which comprises the end region, which end region is arranged at a maximum distance from the at least one plane of symmetry.

11. The respiratory mask of claim 1, wherein an end region of the guide groove is arranged spatially adjacent to the receiving element, the receiving element spanning an end region of the guide groove in such a way that a receiving space is formed.

12. The respiratory mask of claim 1, wherein the receiving element comprises two webs, a bridge, a receiving diameter Y and a receiving opening X, the bridge being produced in one piece with the two webs and being arranged spatially separate from a groove bottom, and the two webs, the bridge and the groove bottom delimiting a receiving space.

13. The respiratory mask of claim 12, wherein the two webs are arranged at an angle & ranging from 30° to 90° to the groove bottom.

14. The respiratory mask of claim 12, wherein the bridge is at least in part circular with the receiving diameter Y, and is interrupted by the receiving opening X.

15. The respiratory mask of claim 12, wherein the receiving element comprises at least one central web and at least one aperture, the central web being arranged between the bridge and the outer side.

16. The respiratory mask of claim 12, wherein the receiving opening X is oriented to the front.

17. The respiratory mask of claim 1, wherein the connection element is a releasable part of the respiratory mask, the receiving element being configured and designed to releasably receive the connection element via a fastening element integrally formed on the connection element.

* * * * *